(12) United States Patent
Strauss et al.

(10) Patent No.: US 7,662,570 B2
(45) Date of Patent: Feb. 16, 2010

(54) LABOR BIOMARKERS, METHODS COMPRISING SAME, AND METHODS TARGETING SAME

(75) Inventors: Jerome F. Strauss, Wyndmoor, PA (US); Mary D. Sammel, Wallingford, PA (US); Rita Leite, Boothwyn, PA (US); Amy Brown, Swarthmore, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 314 days.

(21) Appl. No.: 11/339,816

(22) Filed: Jan. 26, 2006

(65) Prior Publication Data

US 2006/0166280 A1 Jul. 27, 2006

Related U.S. Application Data

(60) Provisional application No. 60/646,589, filed on Jan. 26, 2005.

(51) Int. Cl.
*G01N 33/53* (2006.01)

(52) U.S. Cl. .......... 435/7.1; 436/517; 436/536
(58) Field of Classification Search ............... None
See application file for complete search history.

(56) References Cited

OTHER PUBLICATIONS

Tucker H., et al. (1988) "Nonsteroidal Antiandrogens. Syntghesis and sturcture-Activity Relationships of 3-substituted derivatives of 2-Hydroxpropionanilides" Journal of Medicinal Chemistry, American Chemial Society, vol. 31, No. 5, pp. 954-959.

*Primary Examiner*—Jacob Cheu
(74) *Attorney, Agent, or Firm*—Mark S. Cohen; Pearl Cohen Zedek Latzer, LLP

(57) ABSTRACT

The present invention provides methods of predicting or detecting labor in a female subject and methods of testing a compound for an ability to delay the onset of labor. The present invention also provides methods of testing a labor marker useful in the diagnostic methods, isolated peptides identified in the present invention, methods for inhibiting labor, utilizing the peptides, and kits comprising methods of the present invention.

6 Claims, 15 Drawing Sheets

Multi-variant Analysis of Amnion Peaks

A. Amnion Peaks

| M/Z | P-Value |
|---|---|
| 2487.018 | 0.000791 |
| 2529.036 | 0.008498 |
| 2928.19 | 0.00394 |
| 3199.046 | 0.00326 |
| 3214.835 | 6.56E-05 |
| 320.468 | 6.98E-05 |
| 3346.415 | 0.033258 |
| 3376.546 | 0.002962 |
| 3445.389 | 0.000791 |
| 3712.676 | 0.019494 |
| 4023.371 | 8.4E-05 |
| 4124.58 | 0.033258 |
| 4138.394 | 0.000101 |
| 4630.164 | 0.026578 |
| 4968.309 | 0.017299 |
| 4983.209 | 0.002962 |
| 9480.2 | 0.023696 |

B. Decision Tree Based on Statistically Significant Peaks

Analysis of Cervicovaginal Secretions

A. Cervicovaginal Secretion Peaks

| M/Z | P-Value |
|---|---|
| 1799.38 | 0.00379 |
| 1869.747 | 0.000173 |
| 2022.473 | 0.00485 |
| 2846.384 | 0.006677 |
| 2911.647 | 0.009102 |
| 3153.793 | 0.002086 |
| 3198.369 | 0.000389 |
| 3228.482 | 0.00379 |
| 3250.459 | 0.041911 |
| 3277.181 | 0.002705 |
| 3309.043 | 0.00982 |
| 3329.248 | 0.009102 |
| 3783.541 | 0.02846 |
| 3852.221 | 0.047453 |
| 3908.649 | 0.036928 |
| 4738.458 | 0.017622 |
| 4893.669 | 0.026625 |
| 5072.664 | 0.00122 |
| 5434.641 | 0.010587 |
| 6184.765 | 0.018906 |
| 6606.413 | 0.010587 |
| 7051.434 | 0.000925 |
| 7240.973 | 0.036928 |
| 7343.981 | 0.034631 |
| 9807.214 | 0.00122 |

B. Decision Tree Based on Statistically Significant Peaks

Labor = intercept + hemo + inten1 vs. labor = intercept + hemo + inten2 phat_h1 = hemo + intens1
phat_h2 = hemo + intens2

|  | ROC | | | Asymptotic Normal |
| --- | --- | --- | --- | --- |
|  | Obs | Area | Std. Err. | [95% Conf. Interval] |
| phat_h1 | 41 | 0.8833 | 0.0531 | 0.77924   0.98743 |
| Inten1 | 41 | 0.8976 | 0.0505 | 0.79869   0.99655 |

Ho: area(phat_h1) = area(phat_h2)
chi2(1) =   0.21     Prob>chi2 =   0.6502

Labor = intercept + hemo vs. labor = intercept + hemo + inten2 roccomp labor: hemo vs. phat_h2

|  | ROC | | -Asymptotic Normal-- | |
| --- | --- | --- | --- | --- |
| | Obs | Area | Std. Err. | [95% Conf. Interval] |
| hemo | 41 | 0.8060 | 0.0683 | 0.67207  0.93983 |
| phat_h2 | 41 | 0.8976 | 0.0505 | 0.79869  0.99655 |

Ho: area(hemo) = area(phat_h2)
  chi2(1) =  3.89    Prob>chi2 =  0.0486

Labor = intercept + inten2 vs. labor = intercept + hemo + inten2 roccomp labor: inten2 vs. phat_h2

|  | Obs | ROC Area | Std. Err. | --Asymptotic Normal-- [95% Conf. Interval] | |
|---|---|---|---|---|---|
| inten2 | 41 | 0.8476 | 0.0666 | 0.71714 | 0.97809 |
| phat_h2 | 41 | 0.8976 | 0.0505 | 0.79869 | 0.99655 |

Ho: area(inten2) = area(phat_h2)
   chi2(1) = 0.91   Prob>chi2 = 0.3399

| Sample # | Hemoglobin Score | Labor (1) or No Labor (0) | Peak Intensity | |
|---|---|---|---|---|
| | | | 3.198 kDa | 1.869 kDa |
| 1 | 2 | 0 | 1.3654 | 0.1841 |
| 7 | 1 | 0 | 0.8936 | 0.2096 |
| 9 | 2 | 0 | 0.7495 | 0.2388 |
| 13 | 1 | 0 | 0.7651 | 0.3628 |
| 19 | 0 | 0 | 0.0538 | 0.2058 |
| 31 | 0 | 0 | 0.1627 | 0.098 |
| 32 | 1 | 0 | 0.3454 | -0.0924 |
| 34 | 3 | 0 | 0.2746 | 1.5772 |
| 35 | 2 | 0 | -0.3998 | 0.1309 |
| 46 | 1 | 0 | 0.1407 | 0.3092 |
| 57 | 2 | 0 | 0.465 | -0.1459 |
| 62 | 1 | 0 | 2.6541 | 0.1987 |
| 63 | 1 | 0 | -0.1853 | -0.8789 |
| 64 | 1 | 0 | 0.3277 | 0.2353 |
| 65 | 0 | 0 | -0.2469 | 0.0654 |
| 66 | 2 | 0 | 0.217 | 0.4822 |
| 68 | 2 | 0 | 0.8775 | 0.149 |
| 70 | 1 | 0 | 0.5456 | -0.0913 |
| 71 | 3 | 0 | 1.13 | 0.3324 |
| 72 | 1 | 0 | 0.3491 | 0.5602 |
| 2 | 1 | 1 | 0.9998 | 0.3749 |
| 3 | 3 | 1 | 1.6234 | 0.5646 |
| 4 | 2 | 1 | 2.1953 | 0.5287 |
| 5 | 2 | 1 | 0.5115 | 0.6934 |
| 6 | 2 | 1 | 0.3649 | 0.4164 |
| 14 | 3 | 1 | 1.2013 | 0.5297 |
| 15 | 3 | 1 | 6.3643 | 3.6116 |
| 17 | 3 | 1 | 12.8613 | 2.3736 |
| 18 | 2 | 1 | 5.1596 | 3.9209 |
| 20 | 3 | 1 | 3.0437 | 0.1658 |
| 25 | 3 | 1 | 6.4219 | 5.9374 |
| 30 | 3 | 1 | 13.2507 | 5.4946 |
| 36 | 3 | 1 | -0.2973 | -0.1922 |
| 41 | 3 | 1 | 41.2945 | 8.142 |
| 44 | 3 | 1 | 9.7426 | 1.5224 |
| 45 | 3 | 1 | 24.5453 | 8.8463 |
| 51 | 3 | 1 | 1.0513 | 0.7354 |
| 52 | 2 | 1 | 0.4401 | 0.3917 |
| 54 | 3 | 1 | 6.7594 | 2.966 |
| 55 | 0 | 1 | 9.9264 | 2.66 |
| 56 | 1 | 1 | -0.0305 | 0.0033 |

LABOR BIOMARKERS, METHODS COMPRISING SAME, AND METHODS TARGETING SAME

CROSS REFERENCE TO RELATED APPLICATION

This application claims priority of U.S. Provisional Application Ser. No. 60/646,589, filed Jan. 26, 2005. This application is hereby incorporated in its entirety by reference herein.

STATEMENT REGARDING FEDERALLY SPONSORED RESEARCH OR DEVELOPMENT

The invention described herein was supported in part by grants from the Fogarty International Center (Grant No. D43TW000671) and the National Institutes of Child Health and Human Development (Grant Nos. T32HD007305 and R01-HD034612). The government has certain rights in the invention.

FIELD OF THE INVENTION

The present invention provides methods of predicting or detecting labor in a female subject and methods of testing a compound for an ability to delay the onset of labor. The present invention also provides methods of testing a labor marker useful in the diagnostic methods, isolated peptides identified in the present invention, methods for inhibiting labor, utilizing the peptides, and kits used to perform methods of the present invention

BACKGROUND OF THE INVENTION

Effective management strategies for identifying and treating preterm labor are required to prevent preterm birth. Early births resulting from preterm labor result in a heavy burden of infant mortality and morbidity. Preterm birth is a factor in three-quarters of neonatal mortality and one-half of long-term neurologic impairment in children.

Early detection and management of preterm labor helps to prevent preterm birth and its potential neonatal sequelae, which include respiratory distress syndrome, sepsis, intraventricular hemorrhage, necrotizing enterocolitis, patent ductus arteriosus, and hyperbilirubinemia; however, widespread treatment of women with signs and symptoms of preterm labor has not significantly reduced the prevalence of preterm birth in the United States, underscoring the need to improve current methods for detecting preterm labor.

SUMMARY OF THE INVENTION

The present invention provides methods of predicting or detecting labor, either full-term labor or preterm labor, comprising the assaying of a biological fluid for the presence of marker proteins or peptides. Measuring one or more marker proteins or peptides, and comparing their amounts to reference standards, predicts the pregnancy status of the subject.

In one embodiment, depicted in FIG. 4B, right branch, the present invention provides a method of predicting or detecting labor in a female subject, comprising (a) determining an amount of a first peptide in a biological sample of the female subject, the first peptide having an amino acid sequence set forth in SEQ ID No: 10; (b) comparing the amount of a first peptide to a reference standard for the first peptide; (c) determining an amount of a second peptide, the second peptide having an amino acid sequence set forth in SEQ ID No: 7, wherein the amount is an amount in the biological sample wherein the first peptide was detected or an additional biological sample of the female subject; and (d) comparing the amount of a second peptide to a reference standard for the second peptide.

Attainment of outcome (i) indicates, in this embodiment, that the female subject is in labor. Outcome (i) is defined, in this embodiment, as both (i a) the amount of a first peptide is higher than an upper limit of a range defined by the reference standard for the first peptide; and (i b) the amount of a second peptide is higher than an upper limit of a range defined by the reference standard for the second peptide.

Attainment of outcome (ii) indicates, in this embodiment, that the female subject is not in labor. Outcome (ii) is defined, in this embodiment, as both (ii a) the amount of a first peptide is higher than an upper limit of a range defined by the reference standard for the first peptide; and (ii b) the amount of a second peptide is lower than a lower limit of a range defined by the reference standard for the second peptide.

In another embodiment, the present invention provides a method of predicting or detecting labor in a female subject, comprising (a) determining an amount of a first peptide in a biological sample of the female subject, the first peptide having an amino acid sequence set forth in SEQ ID No: 10; (b) comparing the amount of a first peptide to a reference standard for the first peptide; (c) determining an amount of a hemoglobin-derived peptide, wherein the amount is an amount in the biological sample wherein the first peptide was detected or an additional biological sample of the female subject; and (d) comparing the amount of a second peptide or protein to a reference standard for the second peptide or protein. In another embodiment, the hemoglobin-derived peptide has an amino acid sequence selected from the sequences set forth in SEQ ID No: 8, 9, 11, and 12. Each possibility represents a separate embodiment of the present invention.

Attainment of outcome (i) indicates, in this embodiment, that the female subject is in labor. Outcome (i) is defined, in this embodiment, as both (i a) the amount of a first peptide is higher than an upper limit of a range defined by the reference standard for the first peptide; and (i b) the amount of a hemoglobin-derived peptide is within a labor range defined by the reference standard for the hemoglobin-derived peptide.

Attainment of outcome (ii) indicates, in this embodiment, that the female subject is not in labor. Outcome (ii) is defined, in this embodiment, as both (ii a) the amount of a first peptide is higher than an upper limit of a range defined by the reference standard for the first peptide; and (ii b) the amount of a hemoglobin-derived peptide is within a non-labor range defined by the reference standard for the hemoglobin-derived peptide.

In another embodiment, the present invention provides a method of testing a compound for an ability to delay labor onset, comprising (a) determining a clinical state of a first pregnant subject by the method of the present invention, wherein the first pregnant subject has been contacted with the compound; (b) determining a clinical state of a second pregnant subject by the method of the present invention, wherein the second female subject has not been contacted with the compound; and (c) comparing the clinical state of a first pregnant subject to the clinical state of a second pregnant subject, whereby a decreased incidence of the labor onset in the first pregnant subject relative to the second pregnant subject indicates that the compound has an ability to delay an onset of a labor.

In another embodiment, the present invention provides an isolated peptide having an amino acid sequence selected from the sequences set forth in SEQ ID No: 1-6. Each peptide represents a separate embodiment of the present invention.

In another embodiment, the present invention provides an isolated peptide having an amino acid sequence selected from the sequences set forth in SEQ ID No: 7-12. Each peptide represents a separate embodiment of the present invention.

In another embodiment, the present invention provides a method for inhibiting induction of labor in a subject, comprising contacting the subject with a compound or antibody that prevents an interaction between a peptide having an amino acid sequence set forth in SEQ ID No: 9 and a receptor of the peptide.

In another embodiment, the present invention provides a method for arresting labor in a subject, comprising contacting the subject with a compound or antibody that prevents an interaction between a peptide having an amino acid sequence set forth in SEQ ID No: 9 and a receptor of the peptide.

In another embodiment, the present invention provides a method for inhibiting induction of labor in a subject, comprising contacting the subject with a compound or antibody that interacts with a peptide having an amino acid sequence set forth in SEQ ID No: 9.

In another embodiment, the present invention provides a method for arresting labor in a subject, comprising contacting the subject with a compound or antibody that interacts with a peptide having an amino acid sequence set forth in SEQ ID No: 9.

BRIEF DESCRIPTION OF THE DRAWINGS

FIG. 8. Raw data for combined term and preterm labor samples.

DETAILED DESCRIPTION OF THE INVENTION

The present invention provides methods of predicting or detecting labor, either full-term labor or preterm labor, comprising the assaying of a biological fluid for the presence of marker proteins or peptides. Measuring one or more marker proteins or peptides, and comparing their amounts to reference standards, predicts the labor status of the subject.

As provided herein, the findings of Examples 2 and 4 show that various proteins and peptides correlate with the labor status of a subject.

Figure 4:
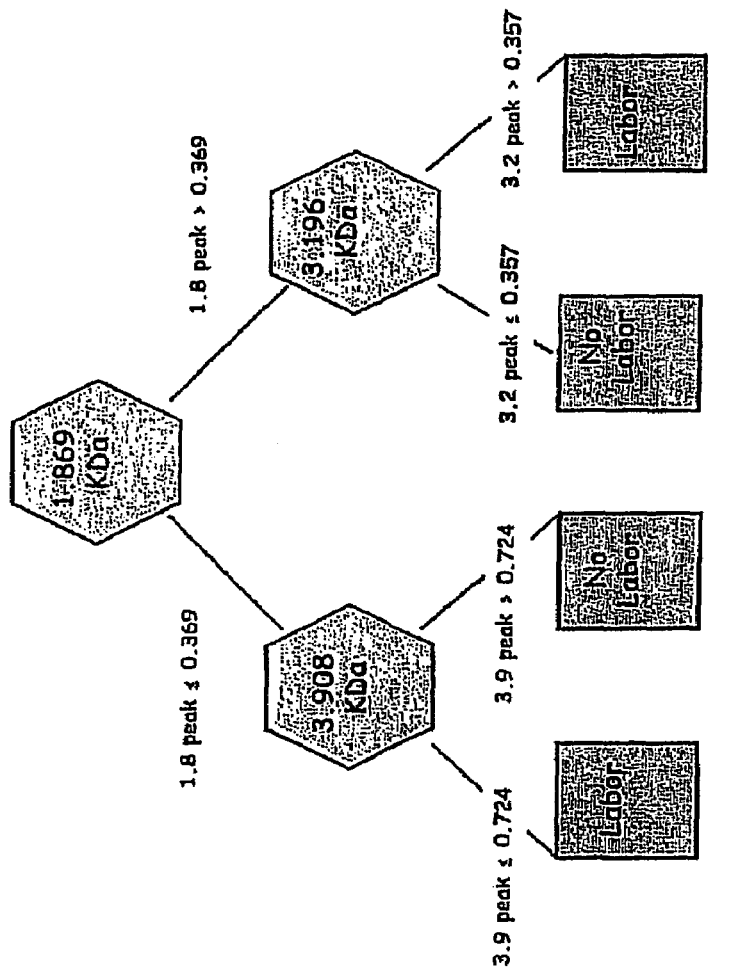
FIG. 4. Analysis of Cervicovaginal Secretions. Spectra from each sample were collected, normalized by the total ion current, and analyzed using Biomarker Wizard software. A) Molecular weight and respective p-values of the 25 peaks found to be statistically different between cervicovaginal secretions collected at term from patients experiencing labor and patients who are not in labor. B) An example of a decision tree established by the CART software program. CART was used to analyze the 25 peaks and establish decision trees based on peak data. This 4-noded tree correctly classified 95% no labor and 100% of labored cervicovaginal secretion samples. Peaks utilized in the decision tree are indicated by hexagons. Sorting mechanism based on the intensity of specific peaks is indicated on each diagonal line. Terminal nodes are indicated by the colored squares FIG. 5. Cervicovaginal Peak Identities. Several statistically significant peaks were chosen to be identified using PCI-QTOF. Each portion of the figure corresponds to a specific peak and contains a bar graph indicating the average intensity levels (and standard errors) in the labor and no labor samples, a typical spectrum, and the identity of the peak. The 1.869 kDa peak (A) and 1 peptide contained in the 3.277 kDa peak (E) were identified as fragments of β-chain hemoglobin, and the 3.196 kDa peak (C) and the 3.228 kDa peak (D) have identical amino acids sequences, but the increased MW of the 3.228 kDa peak is due to oxidized tryptophan and histidine residues. 2.022 kDa peak (B), the 3.196 kDa peak (C), the 3.228 kDa peak (D), were all identified as fragments of α-chain hemoglobin.

In one embodiment, depicted in FIG. 4B, right branch, the present invention provides a method of predicting or detecting labor in a female subject, comprising (a) determining an amount of a first peptide in a biological sample of the female subject, the first peptide having an amino acid sequence set forth in SEQ ID No: 10; (b) comparing the amount of a first peptide to a reference standard for the first peptide; (c) determining an amount of a second peptide, the second peptide having an amino acid sequence set forth in SEQ ID No: 7, wherein the amount is an amount in the biological sample wherein the first peptide was detected or an additional biological sample of the female subject; and (d) comparing the amount of a second peptide to a reference standard for the second peptide.

Attainment of outcome (i) indicates, in this embodiment, that the female subject is in labor. Outcome (i) is defined, in this embodiment, as both (i a) the amount of a first peptide is higher than an upper limit of a range defined by the reference standard for the first peptide; and (i b) the amount of a second peptide is higher than an upper limit of a range defined by the reference standard for the second peptide.

Attainment of outcome (ii) indicates, in this embodiment, that the female subject is not in labor. Outcome (ii) is defined, in this embodiment, as both (ii a) the amount of a first peptide is higher than an upper limit of a range defined by the reference standard for the first peptide; and (ii b) the amount of a second peptide is lower than a lower limit of a range defined by the reference standard for the second peptide.

In another embodiment, depicted in FIG. 4B, left branch, the present invention provides a method of predicting or detecting labor in a female subject, comprising (a) determining an amount of a first peptide in a biological sample of the female subject, the first peptide having an amino acid sequence set forth in SEQ ID No: 10; (b) comparing the amount of a first peptide to a reference standard for the first peptide; (c) determining an amount of a second protein or peptide, the second protein or peptide having a molecular mass of about 3.908 kilodaltons (kDa), wherein the amount is an amount in the biological sample wherein the first peptide was detected or an additional biological sample of the female subject; and (d) comparing the amount of a second protein or peptide to a reference standard for the second protein or peptide. The diagnosis is made based on the outcome of assessing the levels of the four proteins, as will now be described:

Attainment of outcome (i) indicates, in this embodiment, that the female subject is in labor. Outcome (i) is defined, in this embodiment, as both (i a) the amount of a first peptide is lower than a lower limit of a range defined by the reference standard for the first peptide; and (i b) the amount of a second protein or peptide is lower than a lower limit of a range defined by the reference standard for the second protein or peptide.

Attainment of outcome (ii) indicates, in this embodiment, that the female subject is not in labor. Outcome (ii) is defined, in this embodiment, as both (ii a) the amount of a first peptide is lower than a lower limit of a range defined by the reference standard for the first peptide; and (ii b) the amount of a second protein or peptide is higher than an upper limit of a range defined by the reference standard for the second protein or peptide.

"Labor" in methods of the present invention refers, in one embodiment, to cervical dilation. In another embodiment, "labor" refers to cervical effacement. In another embodiment, "labor" refers to latent phase labor. In another embodiment, "labor" refers to active phase labor. In another embodiment, "labor" refers to uterine contractions. In another embodiment, "labor" refers to rupture of membranes. In another embodiment, "labor" refers to any other definition thereof in the art. Each definition of labor represents a separate embodiment of the present invention.

The peptide of SEQ ID No: 7 was found in several oxidation states in amnion and cervicovaginal fluids (Examples 2 and 4). In one embodiment of methods of the present invention, this peptide does not comprise any oxidized amino acids. In another embodiment, this peptide does comprise one or more oxidized amino acids. Each oxidation state of the peptide represents a separate embodiment of the present invention.

Methods of defining a range using a reference standard are well known in the art. In one embodiment of methods of the present invention, the range is defined using a statistical method. In one embodiment, the statistical method is a CART analysis method. In another embodiment, the statistical method is any other statistical method known in the art. In another embodiment, the range is defined by an empirical determination of the best range to use for classifying the subjects; for example, by comparing the predictive power of methods utilizing different ranges. Each method of determining the range of values represents a separate embodiment of the present invention.

In one embodiment, a range of values of a method of the present invention has both an upper and a lower limit For example, a range can be between 5 and 100,000, 10 and 50,000, 20 and 10,000, 100 and 5000, 1 and 1000, 5 and 1000, 10 and 500, 50 and 200, 80 and 100, 0.1 and 5, 0.01 and 1, 0.005 and 0.4, or any other set of two numbers. In another embodiment, the range has only an upper limit; for example, either below, or below or equal to 100,000, 30,000, 10,000, 3000, 1000, 500, 100, 30, 10, 5, 1, 0.5, 0.2, 0.02, 0.005, 0.001, or any other number. In another embodiment, the range has only a lower limit; for example, either above, or above or equal to 100,000, 30,000, 10,000, 3000, 1000, 500, 100, 30, 10, 5, 1, 0.5, 0.2, 0.02, 0.005, 0.001, or any other number. In one embodiment, the range is quantitative (e.g. a range of values). In another embodiment, the range is qualitative. Determining whether an amount falls within a qualitative range is assessed, in one embodiment, by a qualitative method, e.g, a colorimetric assay, the formation of a precipitate, etc, in a method of the present invention. In another embodiment, a range is absolute; e.g, the same for all subjects. In another embodiment, the range is relative. The relative range is determined, in one embodiment, by comparison to an amount of a different protein or peptide in the biological sample. In another embodiment, the relative range is determined by comparison to an internal standard in the biological sample. In another embodiment, the relative range is determined by comparison to an amount of a protein or peptide in a different biological sample from the subject. Each type of range represents a separate embodiment of the present invention.

An "amount" of a marker in a method of the present invention refers, in one embodiment, to an absolute amount in the biological sample. In another embodiment, "amount" refers to a concentration in the sample. In another embodiment, "amount" refers to an amount that is free, e.g, not bound to a component of the sample—for example, the hematocrit, a particular population of cells, or a particular population of proteins, or lipids or other biological molecules. In another embodiment, "amount" refers to an amount that is bound to the component. Each possibility represents a separate embodiment of the present invention.

The peptide detected in methods of the present invention is, in one embodiment, a protein. In another embodiment, the peptide is a fragment of a protein. In another embodiment, the peptide is a proteolytic product of a protein. In another embodiment, the peptide is a hormone. In another embodiment, the peptide is any other type of peptide known in the art. Each type of peptide represents a separate embodiment of the present invention.

In another embodiment, the present invention provides a method of predicting or detecting labor in a female subject, comprising (a) determining an amount of a first peptide in a biological sample of the female subject, the first peptide having an amino acid sequence set forth in SEQ ID No: 10; (b) comparing the amount of a first peptide to a reference standard for the first peptide; (c) determining an amount of a hemoglobin-derived peptide, the hemoglobin-derived peptide, wherein the amount is an amount in the biological sample wherein the first peptide was detected or an additional biological sample of the female subject; and (d) comparing the amount of a second peptide or protein to a reference standard for the second peptide or protein. The findings of Example 3 demonstrate that each of the peptides or proteins of SEQ ID No: 7-12 and each of the other peptides in Tables 1 and 2 are useful in predicting or detecting labor, both individually and in combination. In another embodiment, the hemoglobin-derived peptide has an amino acid sequence selected from the sequences set forth in SEQ ID No: 8, 9, 11, and 12. Each possibility represents a separate embodiment of the present invention.

Attainment of outcome (i) indicates, in this embodiment, that the female subject is in labor. Outcome (i) is defined, in this embodiment, as both (i a) the amount of a first peptide is higher than an upper limit of a range defined by the reference standard for the first peptide; and (i b) the amount of a hemoglobin-derived peptide is within a labor range defined by the reference standard for the hemoglobin-derived peptide.

Attainment of outcome (ii) indicates, in this embodiment, that the female subject is not in labor. Outcome (ii) is defined, in this embodiment, as both (ii a) the amount of a first peptide is higher than an upper limit of a range defined by the reference standard for the first peptide; and (ii b) the amount of a hemoglobin-derived peptide is within a non-labor range defined by the reference standard for the hemoglobin-derived peptide.

As provided herein, the findings of Example 6 show the results of a Chemstrip® urine hemoglobin test can be combined with the amount of a peptide of the present invention to determine the labor status of a subject. In another embodiment, the present invention provides a method of predicting or detecting labor in a female subject, comprising (a) determining an amount of a peptide or protein, wherein the amount is an amount in a biological sample of the female subject; (b) comparing the amount of a peptide or protein to a reference standard for the peptide or protein; (c) administering a hemoglobin test to the female subject; and (d) comparing a result of the hemoglobin test to a reference standard for the hemoglobin test.

Attainment of outcome (i) indicates, in this embodiment, that the female subject is in labor. Outcome (i) is defined, in this embodiment, as both (i a) the amount of a peptide or protein is within a labor range defined by the reference standard for the peptide or protein; and (i b) the result of a hemoglobin test is within a labor range defined by the reference standard for the hemoglobin test.

Attainment of outcome (ii) indicates, in this embodiment, that the female subject is not in labor. Outcome (ii) is defined, in this embodiment, as both (ii a) the amount of a peptide or protein is higher than an upper limit of a range defined by the reference standard for the peptide or protein; and (ii b) the result of a hemoglobin test is within a non-labor range defined by the reference standard for the hemoglobin test.

In another embodiment, the labor ranges and non-labor ranges of the hemoglobin test in a method of the present invention are the same ranges as those used in the other applications of the hemoglobin test. In another embodiment, the labor ranges and non-labor ranges are the same ranges as those used in the other applications of the hemoglobin test. Each possibility represents a separate embodiment of the present invention.

The terms "labor range" and "non-labor range" refer, in one embodiment, to ranges of values or amounts that are observed in subjects in labor and not in labor, respectively. For example, for the 3.908 kDa peptide, the labor-range is, in one embodiment, a peak height of less than or equal to 0.724, and the non-labor range is a peak height of greater than 0.724. In another embodiment, the labor-range for the 3.196 kDa peptide is, in one embodiment, a peak height of greater than 0.357, and the non-labor range is a peak height of less than or equal to 0.357. One skilled in the art will understand that the labor and non-labor ranges can be defined by a wide range of numbers, and will vary according to the assay used, the exact protocol followed, the patient population, and other variables. Each labor range and non-labor range represents a separate embodiment of the present invention.

In one embodiment, the hemoglobin test is a urine hemoglobin test. In another embodiment, the hemoglobin test is a hemoglobin test of any other biological fluid or tissue known in the art. Each hemoglobin test represents a separate embodiment of the present invention.

In one embodiment, a peptide or protein detected in a method of present invention has an amino acid sequence selected from the sequences set forth in SEQ ID No: 7 or 10. In another embodiment, the peptide or protein has an amino acid sequence selected from the sequences set forth in SEQ ID No: 8, 9, 11, and 12. In another embodiment, the peptide or protein is any other peptide or protein identified by a method of the present invention. Each peptide or protein represents a separate embodiment of the present invention.

In another embodiment, the present invention provides a method of predicting or detecting labor in a female subject, comprising (a) determining an amount of one or more peptides or proteins in a biological sample of the female subject, the peptides or proteins having an amino acid sequence selected from the sequences set forth in SEQ ID No: 1-6 and 12; and (b) comparing the amounts of the peptides or proteins to respective reference standards for the peptides or proteins. A decision tree is used, in another embodiment, to classify the samples, similar to the above methods. In another embodiment, one or more of the other peptides or proteins in Table 2 is used instead of the peptides having the sequences set forth in SEQ ID No: 1-6 and 12.

In one embodiment, the peptide or protein detected in a method of present invention has an amino acid sequence set forth in SEQ ID No: 5. In another embodiment, the peptide or protein has an amino acid sequence set forth in SEQ ID No: 6. In other embodiments, the peptide or protein has an amino acid sequence selected from the sequences set forth in SEQ ID No: 1-4 and 7-12. In another embodiment, the peptide or protein is one of the peptides or proteins set forth in Table 2. Each possibility represents a separate embodiment of the present invention.

In another embodiment, methods of the present invention comprise the use of one or more additional markers identified by methods of the present invention (e.g. Example 9), in combination with and/or instead of the proteins and peptides identified in the present invention. In another embodiment, methods of the present invention comprise combining amounts of peptides of the present invention with maternal age, gestational age, reproductive history, serum hCG level, and/or other known factors, to improve their accuracy in predicting and/or detecting the onset of labor (Examples 10-11). Each method represents a separate embodiment of the present invention.

In another embodiment, the present invention provides a method of testing a compound for an ability to delay labor onset, comprising (a) determining a clinical state of a first pregnant subject by the method of the present invention, wherein the first pregnant subject has been contacted with the compound; (b) determining a clinical state of a second pregnant subject by the method of the present invention, wherein the second female subject has not been contacted with the compound; and (c) comparing the clinical state of a first pregnant subject to the clinical state of a second pregnant subject, whereby a decreased incidence of the labor onset in the first pregnant subject relative to the second pregnant subject indicates that the compound has an ability to delay an onset of a labor. In another embodiment, the clinical state that is determined is selected from "in labor" or "not in labor." Each possibility represents a separate embodiment of the present invention.

In one embodiment, multiple female subjects are tested by the above method. The use of multiple female subjects increases, in another embodiment, the statistical significance of the results obtained.

Each method of the present invention for determining a clinical state of a pregnant subject can be used in steps (a) and (b) of the above method of testing a compound for an ability to delay labor onset, and the use of each such method represents a separate embodiment of the present invention.

In another embodiment, the present invention provides a method of testing a marker for an ability to predict or detect labor, comprising (a) determining an amount of the marker in a biological sample from a pregnant subject; (b) determining a labor status of the pregnant subject; (c) repeating steps (a)-(b) for a population of additional pregnant subjects; and (d) ascertaining whether a correlation exists between the amount and the labor status, wherein a presence of the correlation indicates that the marker is useful in predicting or detecting labor. In another embodiment, the labor status is selected from: in labor and not in labor. Each possibility represents a separate embodiment of the present invention.

In another embodiment, the present invention provides a method of testing a marker for an ability to predict or detect labor, comprising (a) determining an amount of the marker in a biological sample from a pregnant subject; (b) determining a clinical factor of the female subject; (c) determining a labor status of the pregnant subject; (d) repeating steps (a)-(c) for a population of additional pregnant subjects; and (e) ascertaining whether a correlation exists between (i). a mathematical function of the amount and the clinical factor; and (ii). the pregnancy status, wherein a presence of the correlation indicates that the marker is useful in predicting or detecting labor. In another embodiment, the labor status is selected from: in labor and not in labor Each possibility represents a separate embodiment of the present invention.

In one embodiment, the marker is a protein. In another embodiment, the marker is a peptide. In another embodiment, the marker is a proteolytic product of a protein or peptide of the present invention. In another embodiment, the marker is a variant of a protein or peptide of the present invention. In another embodiment, the marker is a homologue of a protein or peptide of the present invention. Each possibility represents a separate embodiment of the present invention.

In one embodiment, the clinical factor is maternal age. In another embodiment, the clinical factor is gestational age. In another embodiment, the clinical factor is a reproductive history. In another embodiment, the clinical factor is any other clinical factor known in the art. Each clinical factor represents a separate embodiment of the present invention.

"Labor," in one embodiment, refers to term labor. In another embodiment, "labor" refers to preterm labor. The findings of Example 7 demonstrate that the methods of the present invention can be used to detect or predict both term and preterm labor. In another embodiment, "labor" refers to induced labor. In another embodiment, "labor" refers to spontaneous labor. Each type of labor represents a separate embodiment of the present invention.

In one embodiment, the step of determining the amount of one or more proteins or peptides in a method of the present invention comprises an immunological assay. In one embodiment, the immunological assay is a radio-immunoassay (RIA). In another embodiment, the immunological assay is an enzyme-linked immunosorbent assay (ELISA). In another embodiment, the immunological assay is a sandwich immunoassay. In another embodiment, the immunological assay is any other immunological assay known in the art. In one embodiment, the immunological assay is used in place of the mass spectrometry assays described in the Examples, once sequence information is determined for the marker peptides identified. Each immunological assay represents a separate embodiment of the present invention.

Methods of performing immunological assays are well known in the art, and are described, for example, in *Current Protocols in Immunology*, John Wiley & Sons, 2004. Each immunological assay represents a separate embodiment of the present invention.

In another embodiment, the step of determining the amount of one or more proteins or peptides in a method of the present invention comprises a surface-enhanced laser desorption/ionization (SELDI) assay. In one embodiment, the SELDI utilizes a weak cation exchange (WCX2) chemistry. In another embodiment, the SELDI utilizes an Immobilized Metal Affinity Capture (IMAC) chemistry. In one embodiment, the IMAC chemistry comprises a copper ion. In another embodiment, the chemistry is similar to WCX2 chemistry (e.g. an improved or altered version thereof). In another embodiment, the chemistry is similar to IMAC chemistry. Each possibility represents a separate embodiment of the present invention.

In another embodiment, the step of determining the amount of one or more proteins or peptides in a method of the present invention comprises a mass spectrometry assay. In another embodiment, the step comprises any other method for determining an amount of a peptide that is known in the art. Each possibility represents a separate embodiment of the present invention.

In one embodiment, the biological sample or the additional biological sample utilized in a method of the present invention is a cervicovaginal secretion. In another embodiment, the biological sample or the additional biological sample is a urine sample. In another embodiment, the biological sample or the additional biological sample is a serum sample. In another embodiment, the biological sample or the additional biological sample is a blood plasma sample. In another embodiment, the biological sample or the additional biological sample is a saliva sample. In another embodiment, the biological sample or the additional biological sample is a tissue. In another embodiment, the biological sample or the additional biological sample is a fluid. In another embodiment, the biological sample and the additional biological sample are derived from the same tissue or fluid. In another embodiment, the biological sample and the additional biological sample are derived from different tissues or fluids. In one embodiment, biological samples are derived from three or more different tissues or fluids are utilized. Each possibility represents a separate embodiment of the present invention.

In another embodiment, the step of ascertaining whether a correlation exists in a method of the present invention utilizes a classification and regression tree (CART) analysis. CART analysis was used in Examples of the present invention to identify protein peaks that correlate with labor, and can be similarly used for any other indicator of the status of a subject. Use of CART analysis is well known in the art, and is described, for example, in Vlahou A et al, J Biomed Biotechnol. 2003; 2003(5):308-314.

In another embodiment, the step of ascertaining is performed by any other statistical method known in the art; for example, a Pearson correlation, a canonical correlations analysis, a correspondence analysis, a path analysis, a cluster analysis, an equivalence test, a logistic regression model, a model selection technique, etc. Each statistical method represents a separate embodiment of the present invention.

Using these methods, each of the peaks identified in the present invention can be sequenced to determine the amino acid sequence of the peptide or protein comprising them. In one embodiment, the identification comprises amino acid sequencing, as described in Example 8. In another embodiment, the identification comprises mass determination, as described in Example 2 or Example 4. Immunological or other assays are then developed for detection of each of these proteins, further improving the assays of the present invention.

Methods of protein sequencing are well known in the art, and are described, for example, in Lodish et al, Molecular Cell Biology, Fourth Edition, W. H. FREEMAN, 2000; and Berg et al, Biochemistry, Fifth Edition, 2002). Each protein sequencing method represents a separate embodiment of the present invention.

In another embodiment, the present invention provides an isolated peptide having an amino acid sequence selected from the sequences set forth in SEQ ID No: 1-6. Each peptide represents a separate embodiment of the present invention.

In another embodiment, the present invention provides an isolated peptide having an amino acid sequence selected from the sequences set forth in SEQ ID No: 7-12. Each peptide represents a separate embodiment of the present invention.

In another embodiment, the present invention provides an isolated peptide, selected from the peptides set forth in Table 2 herein.

In another embodiment, the present invention provides a homologue of an isolated peptide having an amino acid set forth in one of the sequences of the present invention. In another embodiment, the present invention provides a variant of an isolated peptide having an amino acid set forth in one of the sequences of the present invention. Each possibility represents a separate embodiment of the present invention.

The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

In another embodiment, "homology" refers to identity to one of SEQ ID No: 1-12 of greater than 70%. In another embodiment, the identity is greater than 75%. In another embodiment, the identity is greater than 80%. In another embodiment, the identity is greater than 82%. In another embodiment, the identity is greater than 85%. In another embodiment, the identity is greater than 86%. In another embodiment, the identity is greater than 87%. In another embodiment, the identity is greater than 88%. In another embodiment, the identity is greater than 89%. In another embodiment, the identity is greater than 90%. In another embodiment, the identity is greater than 91%. In another embodiment, the identity is greater than 92%. In another embodiment, the identity is greater than 93%. In another embodiment, the identity is greater than 94%. In another embodiment, the identity is greater than 95%. In another embodiment, the identity is greater than 96%. In another embodiment, the identity is greater than 97%. In another embodiment, the identity is greater than 98%. In another embodiment, the identity is greater than 99%. In another embodiment, the identity is 100%.

Homology is, in another embodiment, determined by computer algorithm for sequence alignment, by methods well described in the art. In another embodiment, computer algorithm analysis of nucleic acid sequence homology includes the utilization of any number of software packages available, such as, for example, the BLAST, DOMAIN, BEAUTY (BLAST Enhanced Alignment Utility), GENPEPT and TREMBL packages.

In another embodiment, homology is determined is via determination of candidate sequence hybridization, methods of which are well described in the art (See, for example, "Nucleic Acid Hybridization" Hames, B. D., and Higgins S. J., Eds. (1985); Sambrook et al., 1989, Molecular Cloning, A Laboratory Manual, (Volumes 1-3) Cold Spring Harbor Press, N.Y.; and Ausubel et al., 1989, Current Protocols in Molecular Biology, Green Publishing Associates and Wiley Interscience, N.Y). in another embodiment, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. In other embodiments, the FASTA, BLAST, MPsrch or Scanps packages; Smith and Waterman algorithms, and/or global/local or BLOCKS alignments are used. Each method of determining homology represents a separate embodiment of the present invention.

In another embodiment, the present invention provides a proteolytic product of a peptide of the present invention. The findings of Examples 1-4 show that some of the same peptides are found in the amnion and in cervicovaginal secretions. These findings and the findings of Example 5 show that some biomarkers of labor, for the example the 3.2 kDa cluster of α-hemoglobin peptides and other peptides listed above, are stored in the amnion and released with the onset of labor into other biological fluids and tissues, including, for example, cervicovaginal secretions, urine, serum, blood plasma, and saliva. After release from the amnion, the peptides are likely to be undergo additional proteolytic cleavage, thus generating shorter peptides.

In addition, the findings of Example 5 show that peptides depleted in the amnion in subjects in labor are likely to be enriched in other biological fluids and tissues. Thus, in another embodiment, the present invention provides a method of predicting or detecting labor, comprising measuring an amount of one or more of these peptides in one or more biological fluids or tissues. Each peptide represents a separate embodiment of the present invention.

In another embodiment, a peptide detected by a method of the present invention is an indicator of uterine bleeding. In another embodiment, the uterine bleeding is due to decidual hemorrhage. In another embodiment, the uterine bleeding and/or decidual hemorrhage occurs in the course of normal labor. In another embodiment, the uterine bleeding and/or decidual hemorrhage occurs as a pathological event. In another embodiment, the uterine bleeding and/or decidual hemorrhage triggers preterm labor. Each possibility represents a separate embodiment of the present invention.

In another embodiment, the peptide is released or generated as a result of activity of a matrix metalloproteinase (MMP) within the female reproductive tract. In another embodiment, the activity of the MMP helps degrade extracellular matrix proteins in preparation for fetal membrane rupture. In another embodiment, the activity of the MMP helps cause cervical remodeling prior to delivery. In another embodiment, the MMP is a matrixin protein. In another embodiment, the MMP is a collagenase protein. In another embodiment, the presence of the 2.022 kDa peptide in the cervicovaginal secretions during active labor is a consequence of MMP degradation of Hb. Each possibility represents a separate embodiment of the present invention.

In another embodiment, the present invention provides a method for inhibiting induction of labor in a subject, comprising contacting the subject with a compound or antibody that prevents an interaction between a peptide having an amino acid sequence set forth in SEQ ID No: 9 and a receptor of the peptide. The findings of Example 12 show that this peptide exhibits uterotonic potentiating activity, demonstrating that this peptide plays a role in labor induction. Thus, an antagonist of this peptide is useful in preventing labor.

The bradykinin receptor, oxytocin receptor, and prostaglandin receptor are all seven trans-membrane receptors with similar structure. Thus, the findings of Example 12 show that a peptide having an amino acid sequence set forth in SEQ ID No: 9 interacts, under the conditions utilized, with a seven trans-membrane receptor, and that the structure of the receptor for the peptide is likely to resemble one of these receptors. Thus, in one embodiment, the receptor is a seven trans-membrane receptor. In another embodiment, the receptor is a bradykinin receptor. In another embodiment, the receptor is an oxytocin receptor. In another embodiment, the receptor is a prostaglandin receptor. Each possibility represents a separate embodiment of the present invention.

In another embodiment, a peptide of the present invention binds a G-protein coupled receptors (GPCR), which these uterotonic agents bind. In another embodiment, the peptide interacts with a transmembrane domain of a GPCR domains. In another embodiment, the peptide alters GPCR ligand sensitivity.

In another embodiment, the peptide primes cells to become hyper-responsive (in one embodiment, nonspecifically hyper-responsive) to a GCPR agonist. In another embodiment, this priming enhances signal transduction to a heterotrimeric G-protein associated with the GPCR. In another embodiment, the signal transduction augments the release of inositol triphosphate ($IP_3$) from the plasma membrane. In another embodiment, release of $IP_3$ enhances intracellular calcium release. In another embodiment, increased intracellular calcium transients activate calmodulin, which, in turn, activates myosin light chain kinase (MLCK), ultimately increasing smooth muscle contraction (in one embodiment, uterine wall muscle contraction). In another embodiment, the GPCR is an α GPCR. In another embodiment, the GPCR is a β GPCR. In another embodiment, the GPCR is γ GPCR. Each possibility represents a separate embodiment of the present invention.

In another embodiment, a peptide of the present invention activates calcium transients via the cyclic ADP-ribose (cADPR)-signaling pathway. In another embodiment, the peptide activates calcium transients by causing influx of extracellular calcium. In another embodiment, the peptide activates calcium transients by causing mobilization of intracellular calcium. In another embodiment, the calcium transients are utertonin-generated calcium transients. In another embodiment, the peptide potentiates the signaling by bradykinin receptors on decidual cells, those promoting responses that facilitate labor, Each possibility represents a separate embodiment of the present invention, Methods of performing uterine contraction assays are well known in the art, and are described, for example, in (Vane K R et al. Br J Pharmacol. 48:629, 1973) and (Okawa T et al, Am J Obstet Gynecol 184(2): 84-9, 2001). Each method represents a separate embodiment of the present invention.

In another embodiment, the present invention provides a method for arresting labor in a subject, comprising contacting the subject with a compound or antibody that prevents an interaction between a peptide having an amino acid sequence set forth in SEQ ID No: 9 and a receptor of the peptide.

In another embodiment, the present invention provides a method for inhibiting induction of labor in a subject, comprising contacting the subject with a compound or antibody that interacts with a peptide having the amino acid sequence set forth in SEQ ID No: 9. In another embodiment, the compound or antibody inhibits a biological activity of the peptide.

In another embodiment, the present invention provides a method for arresting labor in a subject, comprising contacting the subject with a compound or antibody that interacts with a peptide having the amino acid sequence set forth in SEQ ID No: 9.

In another embodiment, the compound is a small-molecule inhibitor. In another embodiment, the compound is a macromolecule inhibitor. In another embodiment, the compound is itself a peptide. In another embodiment, the compound is any other type of compound or molecule known in the art, for example a peptide, a peptidomimetic, a bivalent polypeptide, a synthetic receptor (Park H et al, Proc Natl Acad Sci USA 99(8): 5105-5109, 2002), etc. In another embodiment, the compound is a competitive inhibitor of the interaction between the peptide and its receptor. In another embodiment, the compound is a non-competitive inhibitor of the interaction. In another embodiment, the compound is a un-competitive inhibitor of the interaction. In another embodiment, the compound inhibits the interaction by any other mechanism known in the art. Each type of inhibitor represents a separate embodiment of the present invention.

Methods of identifying small-molecule inhibitors of peptides, and of their interaction with biological molecules such as proteins, are well known in the art, and are described, for example, in Tanuma S et al (Biol Pharm Bull 27(7): 968-73, 2004; Raimundo B et al (J Med Chem 47(12): 3111-30, 2004; Wang J et al, Proc Natl Acad Sci USA 97(13): 7124-9; 2000; and Huang J et al, (Proc. Natl. Acad. Sci. USA 94: 13396-13401, 1997). Each method represents a separate embodiment of the present invention.

In another embodiment, the inhibitor is tested in a cell-free drug-screening assay. In one embodiment, a cell free drug screening assay is performed by immobilizing either the peptide or its target molecule to a solid matrix (e.g. a bead) facilitate separation of complexes of the peptide and its target molecule from their un-complexed forms, as well as to accommodate automation of the assay. Matrices are then combined, in one embodiment, with the cell lysates (e.g., 35 S-labeled) and the candidate compound, and the mixture incubated under conditions conducive to complex formation (e.g., at physiological conditions for salt and pH). Following incubation, the matrix is washed to remove any unbound label, and immobilized and radiolabel determined either directly, or in the supernatant after the complexes are dissociated, Alternatively, the complexes can be dissociated from the matrix and separated by SDS-PAGE, and the level of target molecule bound to the peptide found in the bead fraction can be quantitated from the gel using standard electrophoretic techniques. For example, either the peptide or its target molecule can be immobilized utilizing conjugation of biotin and streptavidin using techniques well known in the art. Alternatively, antibodies reactive with the peptide but which do not interfere with binding of the material to its target molecule can be derivatized to the wells of the plate, and the peptide trapped in the wells by antibody conjugation. Methods for detecting such complexes include immuno-detection of complexes using antibodies reactive with the target molecule, or which are reactive with the peptide and compete with the target molecule, as well as enzyme-linked assays, which rely on detecting an enzymatic activity associated with the target molecule. Each of these methods represents an additional embodiment of the present invention.

In another embodiment, the peptide is inhibited with an antibody directed against it. Methods of producing antibodies are well known in the art, and are described, for example, in *Current Protocols in Immunology*, Wiley and Sons, eds. Coligan et al. Each method represents a separate embodiment of the present invention.

The term "antibody" refers, in one embodiment, to an antiserum. In another embodiment, "antibody" refers to a purified antibody. In another embodiment, "antibody" refers to a modification of a purified antibody. In another embodiment, the antibody is polyclonal. In another embodiment, the antibody is monoclonal. In another embodiment, the antibody is any other type of antibody known in the art, e.g, a humanized, anti-idiotypic, chimeric, or single chain antibody; an Fab, F(ab').sub.2, Fab expression library fragment, or an epitope-binding fragment of an antibody. Each type of antibody represents a separate embodiment of the present invention.

In one embodiment, the peptide of methods and compositions of the present invention comprises one or more oxidized amino acids. In another embodiment, the peptide does not comprise an oxidized amino acid. In another embodiment, the amounts of one or more peptides with oxidized amino acids are combined with non-oxidized peptides of the same sequence in a diagnostic method of the present invention. In another embodiment, the amounts of one or more peptides with oxidized amino acids are analyzed together with non-oxidized peptides of the same sequence. In another embodiment, one or more peptides with oxidized amino acids are used as alternatives to non-oxidized peptides of the same sequence in methods of the present invention. In another embodiment, an oxidation state of a particular peptide of the present invention, or of a particular amino acid of the peptide, is itself a labor marker. Each possibility represents a separate embodiment of the present invention In another embodiment, the present invention provides a kit comprising a reagent utilized in performing a method of the present invention. In another embodiment, the present invention provides a kit comprising a composition, tool, or instrument of the present invention. In another embodiment, the present invention provides a kit used to perform a method of the present invention. "Kit" refers, in another embodiment, a package that facilitates a diagnostic or other procedure by providing materials or reagents needed thereof in a convenient format. In another embodiment, the kit comprises a means of detecting a peptide of the present invention. Each possibility represents a separate embodiment of the present invention.

EXPERIMENTAL DETAILS SECTION

EXAMPLE 1

A Labor Diagnostic Test Utilizing the Intensity of Amnion Protein Peaks

Materials and Experimental Methods

Collection of Amnion Tissue Samples

Amnion tissue samples were collected from a region distal to the placental insertion, from women either not in labor and undergoing elective cesarean section (CS; n=30); or following normal labor (n=30). All women were between 37 and 42 weeks (Naegele's Rule and/or obstetric ultrasound), and had no vaginal bleeding and intact membranes Samples were washed with phosphate-buffered saline (PBS), and protein homogenates were prepared using a PBS-based lysis buffer containing 0.1% n-octyl-B-D-glucopyranoside, 1 mM sodium vanadate, 2 µg/ml leupeptin, 2 µg/ml apiotinin, and 1 mM PMSF. Samples were centrifuged at 12,000 times gravitational force (xg) (14,000 rpm) for 1 min (minute) and quantitated by BCA protein assay kit (Pierce, Rockford, Ill.) prior to SELDI analysis.

Surface-Enhanced Laser Desorption/Ionization (SELDI) Analysis

Figure 1:
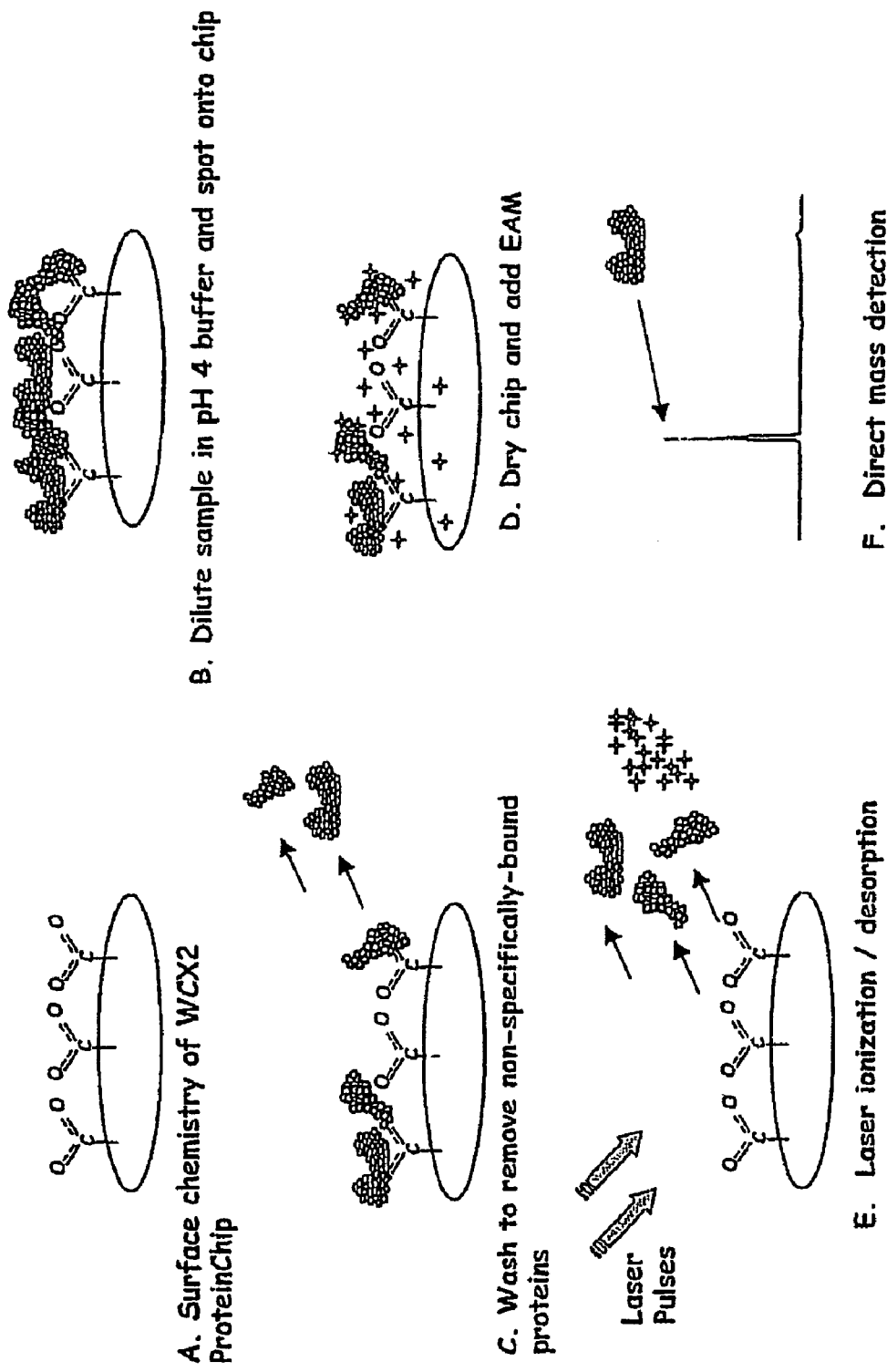
FIG. 1. Surface-enhanced laser desorption/ionization, time-of-flight, mass spectrometry (SELDI-TOF-MS) Biological ProteinChip Array Methodology. A) Each spot had a specific surface chemistry and was exposed to a buffered solution prior to sample spotting. B) Sample was diluted in a buffered solution (pH 4) and spotted onto the chip. C) Extraneous proteins were removed via washing with the pH 4 buffer. D) The chip was dried and energy absorbing molecules (EAM, 20% CHCA) were added to each spot. E) and F) The bound proteins were volatilized with a laser, and direct mass assessments were made using mass spectrometry.

Before loading the samples, 50 µl binding buffer, pH 4 was applied to each spot, and the chip was incubated at room temperature on a platform shaker for 5 minutes. This procedure was performed twice. Samples were diluted in pH 4 buffer (50 mM ammonium acetate, 0.1% Triton X-100, pH=4) to 25 ng/µl protein, and 50 µL of the diluted sample was applied to each spot on a weak cation exchange (WCX2) Protein Chip (Ciphergen), using a 96-well Bioprocessor (Ciphergen Bio-systems, Inc., Fremont, Calif.), a device that holds 12 chips and allows application of larger volumes of serum to each chip array. The Protein-Chip System is an affinity-based mass spectrometric method in which proteins of interest are selectively adsorbed to a chemically modified surface on a biochip. After the samples were incubated at room temperature for 60 minutes on a platform shaker, the array was washed three times with 50 µL of pH 4 buffer for 5 minutes, followed by one rinse with 50 µL of the pH 4 diluted 1 to 100. After air-drying, 0.5 µL of saturated (20%) CHCA (α-cyano-4-hydroxy cinnamic acid; the energy-absorbing molecules [EAM]) in 1:1 acetonitrile: TFA was applied twice to each spot. Surface enhanced laser desorption/ionization time of flight mass spectrometry (SELDI-TOF-MS) was then performed. The method is depicted in FIG. 1.

Spectra were obtained for each sample, normalized using the total ion current, and peak differences and patterns were determined using Biomarker Wizard software (BMW, Ciphergen Biosystems, Inc.) and Classification and Regression Tree software (CART), respectively. Specific peaks of interest were further identified using a Micromass QTOF II (Manchester, UK) tandem quadrupole-time of flight (Q-TOF) mass spectrometer equipped with a PCI 1000 ProteinChip® Tandem MS Interface (Ciphergen Biosystems).

Statistical Analyses.

A p-value of less than 0.05 was used as the criteria for statistical significance of peak intensity differences between groups.

Results

Figure 2:
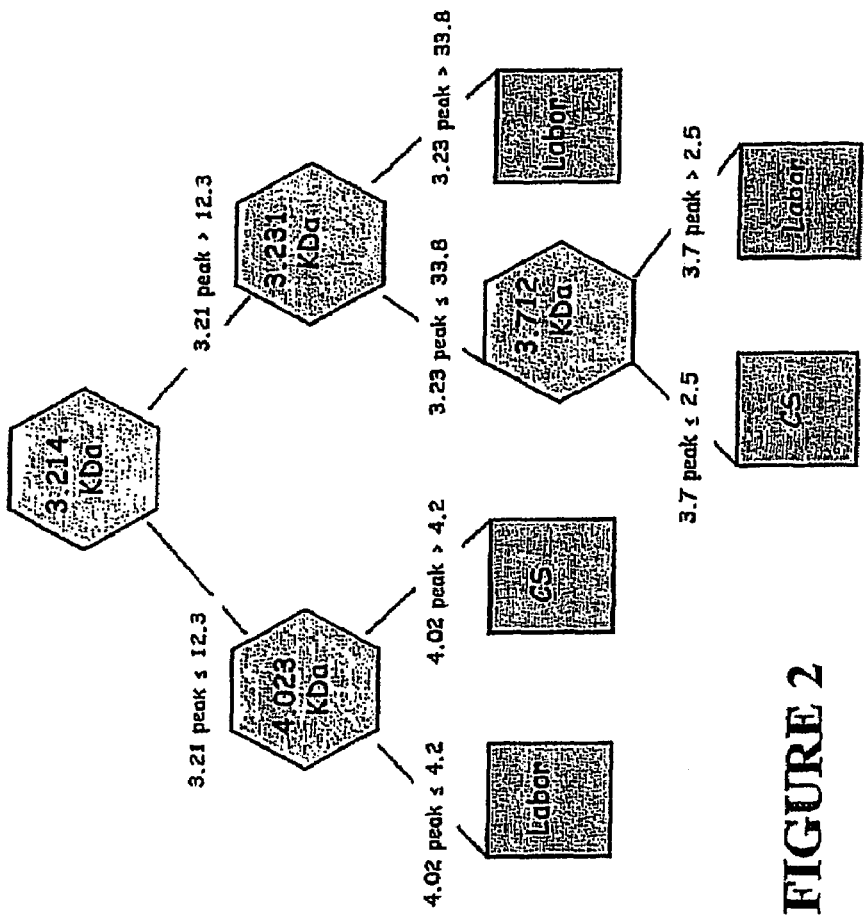
FIG. 2. Multivariate Analysis of Amnion Peaks. Spectra from each sample were collected, normalized by the total ion current, and analyzed using Biomarker Wizard software. A) Molecular weight (as determined by mass/charge (M/Z) ratio) and respective p-values of the 17 peaks found to be statistically significantly different between amnion collected after c-section compared with amnion collected after vaginal delivery. B) An example of a decision tree established by the CART software program. CART was used to analyze the 17 peaks and establish decision trees (also referred to as classification trees) based on peak data. This 5-noded tree correctly classified 96% CS and 90% of labored amnion samples. Peaks utilized in the decision tree are indicated by hexagons. Sorting mechanism based on the intensity of specific peaks is indicated on each diagonal line. Terminal nodes are indicated by the squares.

Amnion tissue samples were collected from women either not in labor and undergoing elective term cesarean section or following normal, term labor, and were analyzed for protein peaks whose intensity differed between the two groups in a statistically significant manner. 17 such peaks were identified, 9 of which were stronger in the CS group, with the other 8 stronger in the labor group. The M/Z (mass/charge ratios) of the peaks are listed in FIG. 2A. CART software was used to develop a classification tree that segregated the samples as either CS or labor, utilizing the 3.214 kDa peak (SEQ ID No: 5), 4.023 kDa peak (SEQ ID No: 12), and 3.712 kDa peak, and the 3.23 kDa peak (SEQ ID No: 6). The classification tree correctly identified 90% of the labor samples and 96% of the CS samples.

EXAMPLE 2

Identification of Peptides Detected in Amnion Protein Peaks Correlated with Labor Materials and Experimental Methods Protein identification was performed by peptide fragmentation, using a tandem mass spectrometer equipped with a PCI-1000 ProteinChip® (Ciphergen) Interface. Single MS and MS/MS spectra were acquired on a tandem mass spectrometer, either a Q-Star® (ABI) or Q-TOF® (Micromass) equipped with a PCI-1000 ProteinChip Interface. Using ProteinChip Arrays as supplied, without further addition of CHCA, spectra were collected in the 1-3 kDa range in single MS mode. After reviewing the spectra, specific ions were selected and introduced into the collision cell for CID fragmentation. The CID spectral data was submitted to the database-mining tool Mascot (Matrix Sciences)®, a search engine that uses mass spectrometry data to identify proteins from primary sequence databases.

Results

Figure 3:
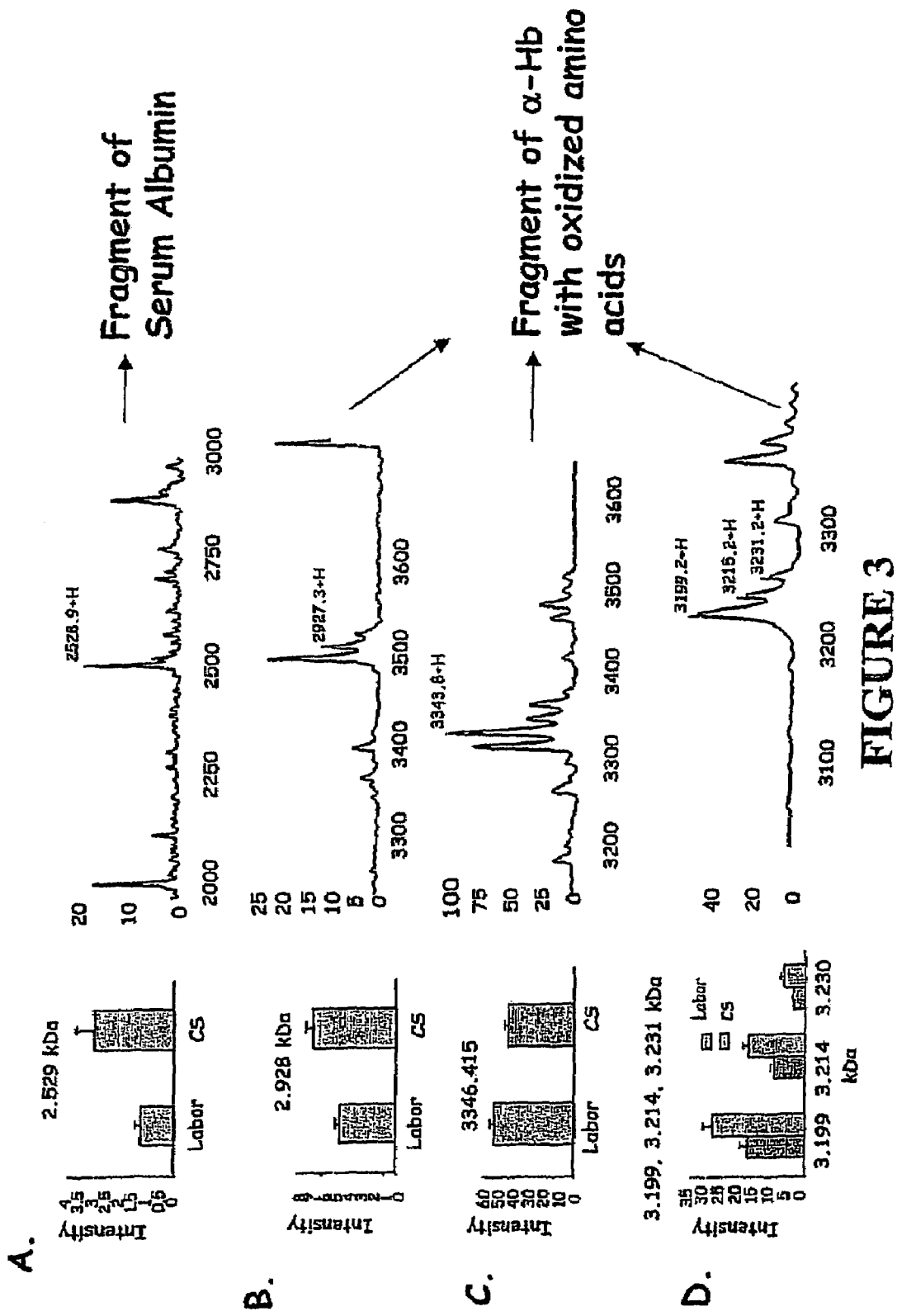
FIG. 3. Amnion Peak Identities. Several statistically significant peaks were chosen to be identified using PCI-QTOF. Each portion of the figure corresponds to a specific peak and contains a bar graph indicating the average intensity levels (and standard errors) in the labor and c-section samples, a typical spectrum, and the identity of the peak. The 2.529 kDa peak (A) was identified as a fragment of serum albumin. The 2.928 kDa peak (B), the 3.346 kDa (C), and the 3.199, 3.214, 3.231 kDa peaks (D) were identified as fragments of the α-chain of hemoglobin with and without oxidized amino acids.

The 3.2 kDa peak cluster and several other peaks from Example 1 were selected for identification. The 3.2 kDa peak cluster, the 3346 kDa peak (corresponding to the 3.343 kDa peak in FIG. 2A), and the 2.927 kDa peak were determined to be fragments of the hemoglobin-α chain with or without oxidized amino acids, while the 2.541 kDa peak (corresponding to the 2.529 kDa peak in FIG. 2A) was determined to be a fragment of serum albumin (FIG. 3). The 2.927 kDa peak was identified by single MS analysis, followed by a search for matches to the mass of human hemoglobin alpha fragments.

The sequences of the identified peptides are depicted in Table 1:

TABLE 1

Sequences of identified amniotic peptides.

| Peak (kDa) | Protein/location | Sequence | SEQ ID No. |
|---|---|---|---|
| 2.541 | Serum albumin AA 24-45 | DAHKSEVAHRFKDLGEENFKAL | 1 |
| 2.927 | Hemoglobin-α AA 1-29 | VLSPADKTNVKAAWGKVGAHAGEYGAEAL | 2 |
| 3.343 | Hemoglobin-α AA 1-32 | VLSPADKTNVKAAWGKVGAHAGEYGAEALERM | 3 |
| 3.199 | Hemoglobin-α AA 1-31 | VLSPADKTNVKAAWGKVGAHAGEYGAEALER | 4 |
| 3.215 | Hemoglobin-α AA | (VLSPADKTNVKAAWGKVGAHAGEYGAEALER)* | 5 |
| 3.231 | Hemoglobin-α AA 1-31 | VLSPADKTNVKAAW*GKVGAH*AGEYGAEALER | 6 |
| 4.023 | | | |
| 3.712 | | | |

*oxidized amino acid.
The 3.215 kDa peptide contains one oxidized amino acid.

Thus, the findings of Examples 1 and 2 show that the amounts of various proteins and peptides in the amnion are indicative of the labor status of pregnant subjects.

EXAMPLE 3

A Labor Diagnostic Test Utilizing the Intensity of Cervicovaginal Secretion Protein Peaks Materials and Experimental Methods Sample Collection Vaginal secretion samples were collected from consenting patients at the Hospital of the University of Pennsylvania, Philadelphia, Pa. All women in the study were pregnant with a normal intra uterine single/twin gestation. Patients within 37 and 42 weeks of pregnancy were classified as term. The gestational age was determined by Nagele's rule and/or obstetric ultrasound. Samples were only collected from patients with intact membranes and without vaginal bleeding. Cervicovaginal secretion samples were collected using a cotton swab prior to the digital examination. The samples were collected in Dulbecco's phosphate buffered saline (DPBS, Invitrogen, Grand Island, N.Y.) containing a protease inhibitor cocktail (Complete Mini®, Roche, Indianapolis, Ind.) and they were immediately flash frozen and stored at −80° C. until further evaluation. Labored and non-labored cervicovaginal secretions were specifically segregated by close observation of uterine contraction and cervical evolution for at least one hour. Patients having none or few contractions, a closed or less than 3 cm dilation of the cervix, and between 0-50% cervical effacement were classified as not in labor (n=20). This diagnosis was contingent upon there being no changes in cervical dilation or effacement after a second evaluation taken approximately one hour later. Patients having active contractions, cervical effacement greater than 50% and dilation greater than 3 cm were classified as in labor if those parameters persisted and were determined in the second evaluation (n=20).

Sample Preparation and Processing

All samples were extensively aliquotted to avoid repetitive freeze-thaw cycles and stored at −80 C. Cervicovaginal fluid protein extracts were cleared via centrifugation at 14,000 rpm at 4 C and quantitated by the BCA protein assay kit (Pierce, Rockford, Ill.). All reagents, equipment and software used during the proteomic analysis of the cervicovaginal secretion samples, unless otherwise indicated, was purchased from Ciphergen Biosystem, Inc., Fremont Calif. Samples were then diluted in pH 4 buffer (50 mM ammonium acetate, 0.1% triton X-100, pH=4) and spotted (25 ng/µl protein) onto weak cation exchange chips (WCX-2). Chips were then dried and spotted twice with energy absorbing molecules (EAM, 20% CHCA) and subsequently analyzed using surface-enhanced laser desorption/ionization, time of flight, mass spectrometry (SELDI-TOF—MS). Spectra were obtained for each sample, normalized using total ion current, and peak differences and patterns were determined using Biomarker Wizard® Software (BMW). Specific peaks were further identified at Ciphergen's Biomarker Discovery Center in Fremont, Calif. using Protein Chip Interface Quadruple Time-of-Flight Mass Spectrometry (PCI-QTOF-MS).

Peptide Synthesis

After receiving peak identities, peptides were manufactured by Genemed Synthesis Inc., San Francisco, Calif. The 2.022 kDa peptide had the following amino acid sequence and was amidated at the C terminus 'N-AAHLPAEFT-PAVHASLDKF-C'. The control peptide was composed of the same amino acids as the 2.022 kDa peptide, but the residues were ordered randomly.

Statistical Analysis

During the proteomic analysis of the cervicovaginal fluids, T-tests were performed to determine statistical differences ($P<0.05$) between the peak intensity of the labored and the unlabored groups. In the cellular contraction studies, results were expressed as the mean±standard error as indicated. Differences between the potentiation and control peptide groups were assessed using a 2-way ANOVA. Additionally, concentration-dependent differences between the values of the potentiating and control peptide were assessed via 1-way ANOVA with a post-test for linear trend. P-values <0.05 were classified as statistically significant.

Results

Cervicovaginal fluid samples were collected from pregnant subjects at full term either in labor (n=20) or not in labor (n=20). 25 protein peaks whose intensity differed between the two groups in a statistically significant manner were identified. 12 of the peaks exhibited greater intensity in non-laboring subjects, while 13 peaks exhibited greater intensity in laboring subjects (FIG. 4A). CART software was used to develop a classification tree that segregated the samples as either CS or labor, utilizing the 1.869 kDa peptide (SEQ ID No: 10), the 3.908 kDa peptide, and the 3.196 kDa peptide (SEQ ID No: 7). The classification tree correctly identified 100% of the labor samples and 95% of the non-labor samples. Several peaks or clusters of peaks, including the 3.2 kDa cluster and the 1.869 kDa, 3.908 kDa, 2.022 kDa, 3.275 kDa, and 3.279 kDa peptides, were particularly useful in classifying the samples.

EXAMPLE 4

Figure 5:
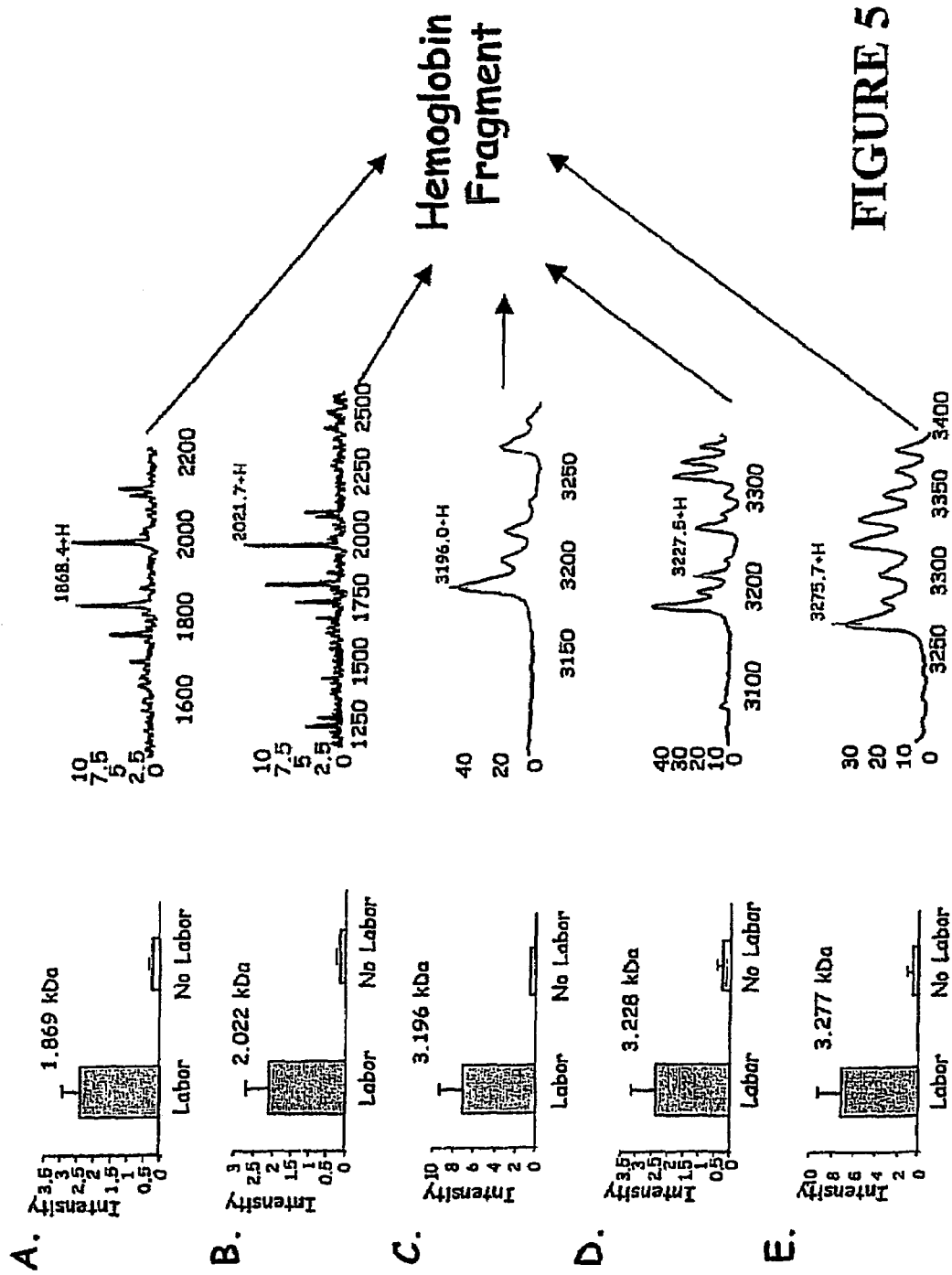

Identification of Peptides Detected in Cervicovaginal Secretion Protein Peaks Correlated with Labor Several peaks from Example 3 were selected for identification. The components of all of the identified peaks were found to be fragments of hemoglobin. The 3.277 kDa peak was found to contain 2 peptides of 3.275 and 3.279 kDa. Specifically, the components of the 3.196 kDa (corresponding to the 3.198 kDa peak of FIG. 4A), 3.228 kDa, 2.022 kDa, and 3.279 (corresponding to the 3.277 kDa peak of FIG. 4A) peaks were fragments of the α-chain, and the components of the 1.869 and 3.275 kDa peaks were fragments of the β-chain of hemoglobin (FIG. 5). The 3.228 kDa peak contained the same peptide as the 3.231 kDa amniotic peptide described above.

The identified peptides are depicted in Table 2. Spectra from each sample were collected, data was normalized by the total ion current, and analyzed using Biomarker Wizard software. Depicted are molecular weight and respective p-values of the peaks that were found to be statistically different ($P<0.05$) between cervicovaginal fluid collected at term from patients experiencing labor and patients who are not in labor.

TABLE 2

Sequences of identified cervicovaginal peptides.

| Peak (kDa) | Protein/ location | Sequence | SEQ ID No. |
|---|---|---|---|
| 3.196 | Hemoglobin-α AA 1-31 | VLSPADKTNVKAAWGKVGAHAGEYGAEALER | 7 |
| 3.228 | Hemoglobin-α AA 1-31 | VLSPADKTNVKAAW*GKVGAH*AGEYGAEALER | 8 |
| 2.022 | Hemoglobin-α AA 110-128 | AAHLPAEFTPAVHASLDKF | 9 |
| 1.869 | Hemoglobin-β AA 130-146 | YQKVVAGVANALAHKYH | 10 |
| 3.279 | Hemoglobin-α AA 5-35 | ADKTNVKAAWGKVGAHAGEYGAEALERMFLS | 11 |
| 3.275 | Hemoglobin-β AA 1-31 | VHLTPEEKSAVTALWGKVNVDEVGGEALGRL | 12 |
| 3.908 | | | |
| 1.799 | | | |
| 2.846 | | | |
| 3.153 | | | |
| 3.250 | | | |
| 3.309 | | | |
| 3.329 | | | |
| 3.783 | | | |
| 3.852 | | | |

TABLE 2-continued

Sequences of identified cervicovaginal peptides.

| Peak (kDa) | Protein/ location | Sequence | SEQ ID No. |
|---|---|---|---|
| 3.908 | | | |
| 4.738 | | | |
| 4.893 | | | |
| 5.072 | | | |
| 5.434 | | | |
| 6.184 | | | |
| 6.606 | | | |
| 7.051 | | | |
| 7.240 | | | |
| 7.343 | | | |
| 9.807 | | | |

*oxidized amino acid.

Thus, the findings of Examples 3-4 show that the amounts of various proteins and peptides in cervicovaginal fluid are markers for the labor status of a subject.

EXAMPLE 5

Inverse Correlations Between Amnion and Cervicovaginal Secretion Protein Peaks

Figure 6:
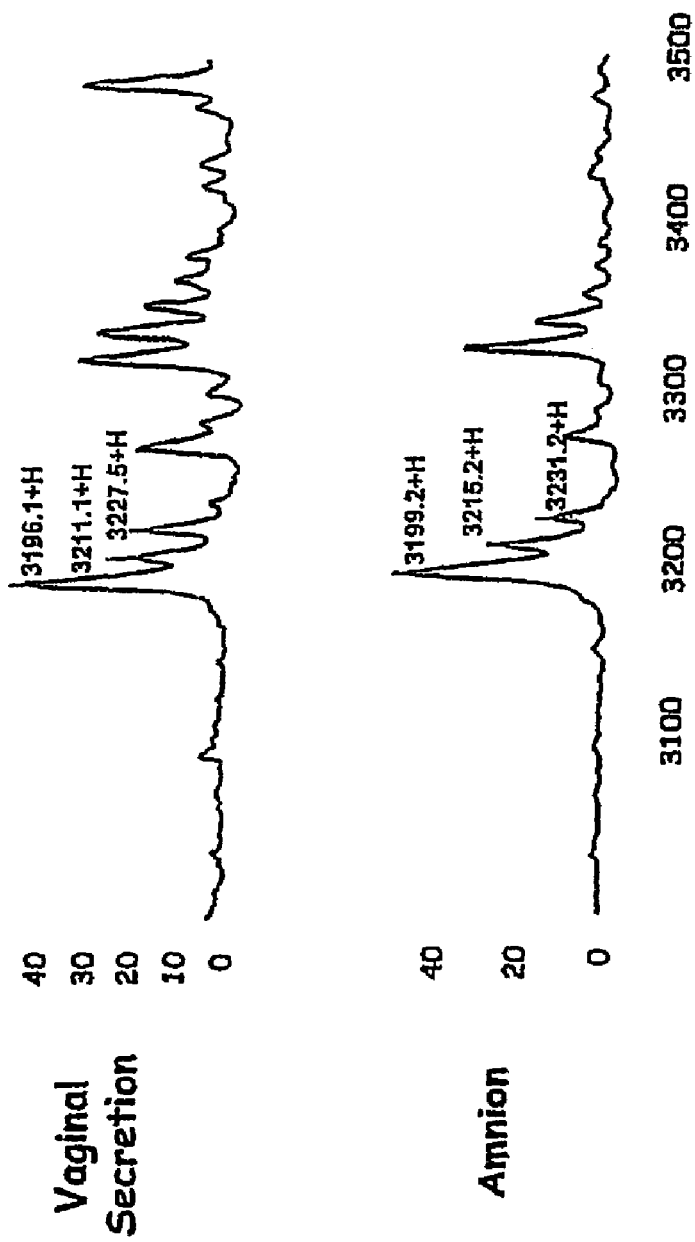
FIG. 6. Amnion and vaginal samples have complementary peak profiles. A number of the peaks exhibited decreased intensity in amniotic tissue as a result of labor and increased intensity in cervicovaginal secretions as a result of labor. For example, peaks in the 3.2 kDa peak cluster were found to be diagnostic for labor in both amniotic tissue and cervicovaginal secretions.

A comparison of the amnion and cervicovaginal secretion protein peak patterns is shown in FIG. 6. A number of the peaks exhibited increased intensity in amniotic tissue samples collected from non-laboring CS subjects than laboring subjects and increased intensity in cervicovaginal samples collected from laboring subjects than non-laboring subjects. The intensity of the 3.2 kDa cluster of α-hemoglobin peptides, for example, was found to be a statistically significant correlate of labor in both the amnion and cervicovaginal secretions.

These findings show that some biomarkers of labor, for the example the 3.2 kDa cluster of α-hemoglobin peptides and other peptides listed above, are stored in the amnion and released with the onset of labor into other biological fluids, including, for example, cervicovaginal secretions, urine, serum, blood plasma, and saliva. The presence of these peptides in various biological fluids can thus be used in diagnosing term and/or preterm labor.

EXAMPLE 6

Refinement of Labor Diagnostic Methods Using the Chemstrip test, and its use in Diagnosing Labor in Both Term and Preterm Subjects Materials and Experimental Methods Inclusion Criteria Pregnant subjects between 22 and 36 weeks, 6 days gestational age suspected of being in preterm labor were recruited, with inclusion criteria otherwise the same as described in Example 1.

Statistical Analyses

Data from the term- and preterm subjects were combined and analyzed in a single group. The Chemstrip® test was performed and evaluated in a blinded manner. The results "negative," "trace," "++," and "+++" were assigned values of 0, 1, 2, and 3, respectively. The proportion of subjects in labor for each of the levels of the Chemstrip® test were computed, and the test of linear trend was conducted for the Chemstrip® test using the Cochran-Armitage trend test. In addition, mean intensity values of the 1.869 kDa and 3.198 kDa peaks were computed for each group. The data are depicted in the tables below:

| | Chemstrip ® test: | | | | |
|---|---|---|---|---|---|
| | Chemstrip ® score. | | | | |
| | 0 | 1 | 2 | 3 | Total |
| Not in labor | 3 | 6 | 9 | 2 | 20 |
| % of non-labor samples with this score | 15.00 | 45.00 | 30.00 | 10.00 | |
| % of samples with this score not in labor | 75.00 | 81.82 | 54.55 | 13.33 | |
| In labor | 1 | 2 | 5 | 13 | 21 |
| % of labor samples with this score | 4.76 | 9.52 | 23.81 | 61.90 | |
| % of samples with this score in labor | 25.00 | 18.18 | 45.45 | 86.67 | |

Cochran-Armitage trend test results:

Statistic (Z) −3.4267

One-sided Pr<Z 0.0003

Two-sided Pr>|Z| 0.0006

| 3.198 kDa and 1.869 kDa peaks | | | | | |
|---|---|---|---|---|---|
| Variable | N | Mean | Std dev | Minimum | Maximum |
| NON-LABOR SUBJECTS | | | | | |
| Peak Intensity 3.198 kDa (inten1) | 20 | 0.524 | 0.676 | −0.3998 | 2.6541 |
| Peak Intensity 1.869 kDa (inten2) | 20 | 0.207 | 0.439 | −0.8789 | 1.5772 |
| LABOR SUBJECTS | | | | | |
| Peak Intensity 3.198 kDa (inten1) | 21 | 7.020 | 9.955 | −0.2973 | 41.2945 |
| Peak Intensity 1.869 kDa (inten2) | 21 | 2.366 | 2.712 | −0.1922 | 8.8463 |

Figure 7A:
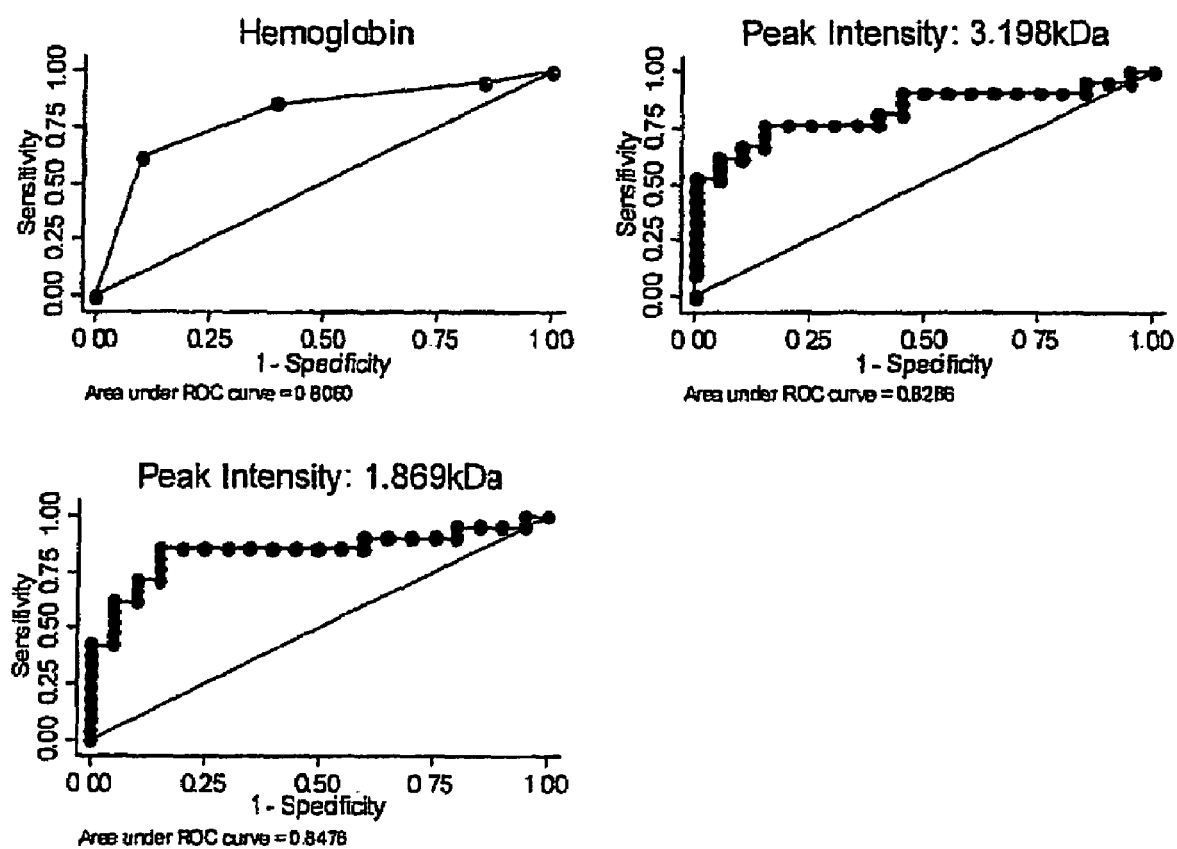
FIG. 7. (A) ROC curves of hemoglobin and the intensity values of the 1.869 kDa and 3.198 kDa peaks. (B) ROC curves of hemoglobin in combination with the intensity values of each of the 1.869 kDa and 3.198 kDa peaks. (C) ROC curves from logistic regression model for predicting labor, comparing the logistic model which combines hemoglobin and intensity of the 3.198 kDa peak ("hemo+intens1"; open circles) vs. hemoglobin and intensity of the 1.869 kDa peak ("hemo+intens2"; closed circles). (D) ROC curves comparing logistic model for hemoglobin alone ("hemo"; open circles) vs. a logistic regression model which combined hemoglobin and intensity of the 1.869 kDa peak ("hemo+intens2"; closed circles). (E) ROC curves from logistic regression model for labor, comparing the combination of hemoglobin and intensity of the 1.869 kDa peak ("hemo+intens2"; open circles) vs. intensity of the 1.869 kDa peak alone ("intens2"; closed circles).

Receiver operating characteristic (ROC) curves were used to ascertain the ability to diagnose labor of the Chemstrip® data and the intensity measures of the 1.869 kDa and 3.198 kDa peaks (referred to as "inten1" and "inten2", respectively). For each level of the marker, the sensitivity as well as specificity were estimated and plotted (FIG. 7A). The area under the ROC curve is reflective of the ability of each marker to assign subjects to the correct category (labor vs non-labor). Comparisons among ROC curves defined for the same set of women were conducted using a non-parametric method described by (DeLong E R et al, Biometrics 44(3): 837-45, 1988). While all three markers exhibited strong diagnostic power, the diagnostic power of the 1.869 kDa peak intensity was the highest. The results are depicted below:

| | ROC | | | Asymptotic Normal | |
|---|---|---|---|---|---|
| | Obs | Area | Std. Err. | [95% Conf. Interval] | |
| Hemoglobin | 41 | 0.8060 | 0.0683 | 0.67207 | 0.93983 |
| Inten1 | 41 | 0.8286 | 0.0682 | 0.69483 | 0.96231 |
| Inten2 | 41 | 0.8476 | 0.0666 | 0.71714 | 0.97809 |

Ho: area(hemo) = area(intensity1) = area(intensity2)
chi2(2) = 0.28 Prob > chi2 = 0.8696

Next, Pearson correlation coefficients were used to ascertain the extent of correlation between the three measures. The results are depicted in the chart below. The Chemstrip measure exhibited a moderate correlation with the other two markers, ($r\_1=0.372$ and $r\_2=0.447$), while the two peak markers were more highly correlated (r=0.865).

| Prob > |r| under H0: Rho = 0 | | | |
|---|---|---|---|
| | hemo | inten1/p-value | inten2/p-value |
| hemo | 1 | 0.37186 | 0.44678 |
| | | 0.0167 | 0.0034 |
| inten1 | 0.37186 | 1 | 0.86491 |
| | 0.0167 | | <.0001 |
| inten2 | 0.44678 | 0.86491 | 1 |
| | 0.0034 | <.0001 | |

Next, combinations of the markers were considered using logistic regression models. All possible combinations of markers were considered, and the best model was selected, using model selection techniques based on the following characteristics: 1) markers included in the model were independent predictors of labor status, as defined by p-value <0.05; 2) there was minimal collinearity of the model parameters, as defined by the correlation among the coefficient estimates; and 3) a statistically significant increase in the area under the ROC curve was observed, as described in DeLong, ibid. The statistics package STATA® was used for all statistical models described.

Univariate analysis was first used to ascertain the predictive power of each variable separately. Hemoglobin was the strongest independent predictor of probability of labor, as depicted below:

A. model: ln[pr(labor)/{1−pr(labor}=intercept+estimate*(hemo).

In this model and all those that follow (B-F), the values for "intercept," "estimate," "estimate1," etc, used in the equation are those found in the "estimate" column of the table labeled "Analysis of Maximum Likelihood Estimates." Thus, in this case the formula used was $$ln[pr(\text{labor})/\{1-pr(\text{labor}\}=-1.324+2.5004*(\text{hemo}).$$

| Testing Global Null Hypothesis: BETA = 0 | | | |
|---|---|---|---|
| Test | Chi-Square | DF | Pr > ChiSq |
| Likelihood Ratio | 13.0202 | 1 | 0.0003 |
| Score | 11.7423 | 1 | 0.0006 |
| Wald | 9.4148 | 1 | 0.0022 |

| Analysis of Maximum Likelihood Estimates | | | | | |
|---|---|---|---|---|---|
| | | | Standard | | |
| Parameter | DF | Estimate | Error | Chi-Square | Pr > ChiSq |
| hemo | 1 | 2.5004 | 0.9249 | 7.3091 | 0.0069 |
| Intercept | 1 | −1.3240 | 0.4315 | 9.4148 | 0.0022 |

B. model: ln[pr(labor)/{1−pr(labor}=intercept+estimate*(inten1)

| Testing Global Null Hypothesis: BETA = 0 | | | |
|---|---|---|---|
| Test | Chi-Square | DF | Pr > ChiSq |
| Likelihood Ratio | 18.8429 | 1 | <.0001 |
| Score | 7.3147 | 1 | 0.0068 |
| Wald | 4.2431 | 1 | 0.0394 |

| Analysis of Maximum Likelihood Estimates | | | | | |
|---|---|---|---|---|---|
| | | | Standard | | |
| Parameter | DF | Estimate | Error | Chi-Square | Pr > ChiSq |
| Intercept | 1 | −1.2249 | 0.5183 | 5.5855 | 0.0181 |
| inten1 | 1 | 0.8634 | 0.4192 | 4.2431 | 0.0394 |

C. model: ln[pr(labor)/{1−pr(labor)}=intercept+estimate*(inten2)

Testing Global Null Hypothesis: BETA = 0

| Test | Chi-Square | DF | Pr > ChiSq |
|---|---|---|---|
| Likelihood Ratio | 17.2493 | 1 | <.0001 |
| Score | 9.8654 | 1 | 0.0017 |
| Wald | 4.2035 | 1 | 0.0403 |

Analysis of Maximum Likelihood Estimates

| Parameter | DF | Estimate | Standard Error | Chi-Square | Pr > ChiSq |
|---|---|---|---|---|---|
| Intercept | 1 | −1.0954 | 0.4974 | 4.8486 | 0.0277 |
| inten1 | 1 | 1.8086 | 0.8821 | 4.2035 | 0.0403 |

Since hemoglobin was the strongest independent predictor of probability of labor, hemoglobin was combined with each of the peak values separately in the following models. The regression coefficient estimates for intens1 and 2 showed significant correlation. Hemoglobin was still a significant predictor even in the presence of the other 2 measures. The results are depicted below:

D. Fit model: ln[pr(labor)/{1−pr(labor)}=intercept+estimate1*(hemo)+estimate2*(inten1)

Testing Global Null Hypothesis: BETA = 0

| Test | Chi-Square | DF | Pr > ChiSq |
|---|---|---|---|
| Likelihood Ratio | 24.4413 | 2 | <.0001 |
| Score | 14.1164 | 2 | 0.0009 |
| Wald | 7.9837 | 2 | 0.0185 |

Analysis of Maximum Likelihood Estimates

| Parameter | DF | Estimate | Standard Error | Chi-Square | Pr > ChiSq |
|---|---|---|---|---|---|
| Intercept | 1 | −3.2451 | 1.1907 | 7.4284 | 0.0064 |
| hemo | 1 | 1.1840 | 0.5491 | 4.6497 | 0.0311 |
| inten1 | 1 | 0.6786 | 0.3625 | 3.5042 | 0.0612 |

Odds Ratio Estimates

| Effect | Point Estimate | 95% Wald Confidence Limits | |
|---|---|---|---|
| hemo | 0.306 | 0.104 | 0.898 |
| inten1 | 0.507 | 0.249 | 1.032 |

E. Fit model: ln[pr(labor){1−pr(labor)}=intercept+estimate1*(hemo)+estimate2*(inten2)

Testing Global Null Hypothesis: BETA = 0

| Test | Chi-Square | DF | Pr > ChiSq |
|---|---|---|---|
| Likelihood Ratio | 22.2498 | 2 | <.0001 |
| Score | 14.9806 | 2 | 0.0006 |
| Wald | 7.5904 | 2 | 0.0225 |

Analysis of Maximum Likelihood Estimates

| Parameter | DF | Estimate | Standard Error | Chi-Square | Pr > ChiSq |
|---|---|---|---|---|---|
| Intercept | 1 | −2.8111 | 1.0609 | 7.0206 | 0.0081 |
| hemo | 1 | 1.0134 | 0.4844 | 4.3771 | 0.0364 |
| inten2 | 1 | 1.5081 | 0.7537 | 4.0031 | 0.0454 |

F. Fit model: ln[pr(labor)/{1−pr(labor)}=intercept+estimate1*(hemo)+estimate2*(inten1)+estimate3*(inten2)

Testing Global Null Hypothesis: BETA = 0

| Test | Chi-Square | DF | Pr > ChiSq |
|---|---|---|---|
| Likelihood Ratio | 24.5784 | 3 | <.0001 |
| Score | 14.9830 | 3 | 0.0018 |
| Wald | 7.6166 | 3 | 0.0546 |

Analysis of Maximum Likelihood Estimates

| Parameter | DF | Estimate | Standard Error | Chi-Square | Pr > ChiSq |
|---|---|---|---|---|---|
| Intercept | 1 | −3.1780 | 1.1902 | 7.1301 | 0.0076 |
| hemo | 1 | 1.1236 | 0.5658 | 3.9437 | 0.0470 |
| inten1 | 1 | 0.5839 | 0.4502 | 1.6820 | 0.1947 |
| inten2 | 1 | 0.3500 | 0.9912 | 0.1247 | 0.7240 |

Estimated Correlation Matrix

| Variable | Intercept | hemo | inten1 | inten2 |
|---|---|---|---|---|
| Intercept | 1 | −0.8764 | −0.3068 | 0.1038 |
| hemo | −0.8764 | 1 | 0.1424 | −0.2623 |
| inten1 | −0.3068 | 0.1424 | 1 | −0.5074 |
| inten2 | 0.1038 | −0.2623 | −0.5074 | 1 |

ROC curves and predicted probabilities were also used to evaluate the predictive power of several variables in isolation and combinations. The ROC curves are depicted in FIG. 7B-E. The resulting pseudo $R^2$ values of all combinations, a measure of the amount of variability in the response (i.e. probability of labor) that is accounted for by the model, are depicted in the table below:

| Pseudo-R2 from STATA | |
| --- | --- |
| Model | Pseudo $R^2$ |
| logistic labor hemo | Pseudo $R^2$ = 0.2292 |
| logistic labor inten1 | Pseudo $R^2$ = 0.3317 |
| logistic labor inten2 | Pseudo $R^2$ = 0.3036 |
| logistic labor hemo inten1 | Pseudo $R^2$ = 0.4302 |
| logistic labor hemo inten2 | Pseudo $R^2$ = 0.3916 |
| logistic labor inten1 inten2 | Pseudo $R^2$ = 0.3522 |
| logistic labor hemo inten1 inten2 | Pseudo $R^2$ = 0.4326 |

Thus, the results of the non-parametric method and the logistic regression models confirmed one another and showed that the hemoglobin value and the intensity of the 1.869 kDa peak were the combination of two variables with the greatest predictive power. Including the intensity of the 3.198 kDa peak slightly increased the pseudo $R^2$ value.

Results

Figure 7B:
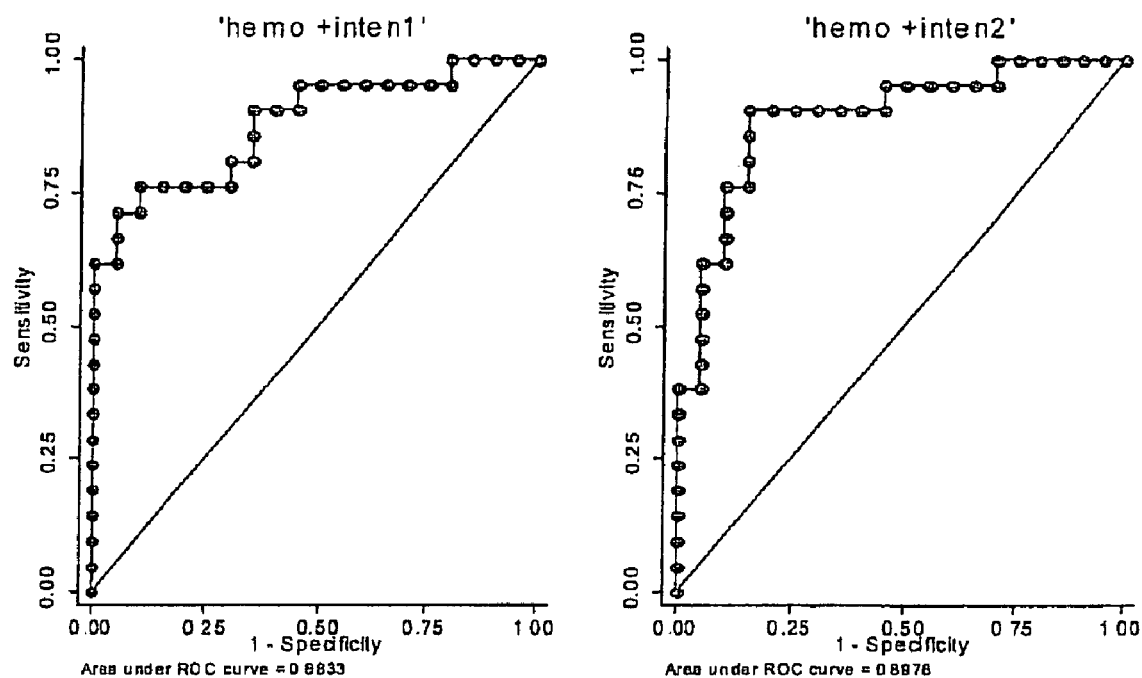
Figure 7C:
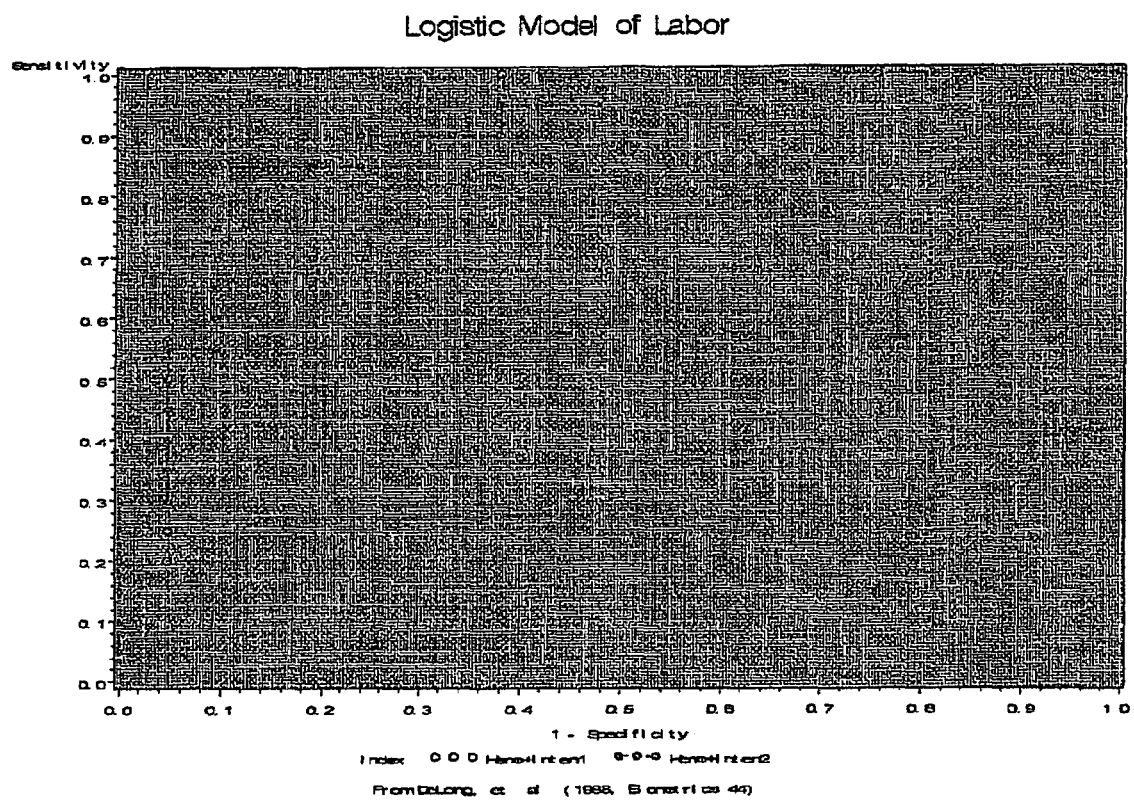
Figure 7D:
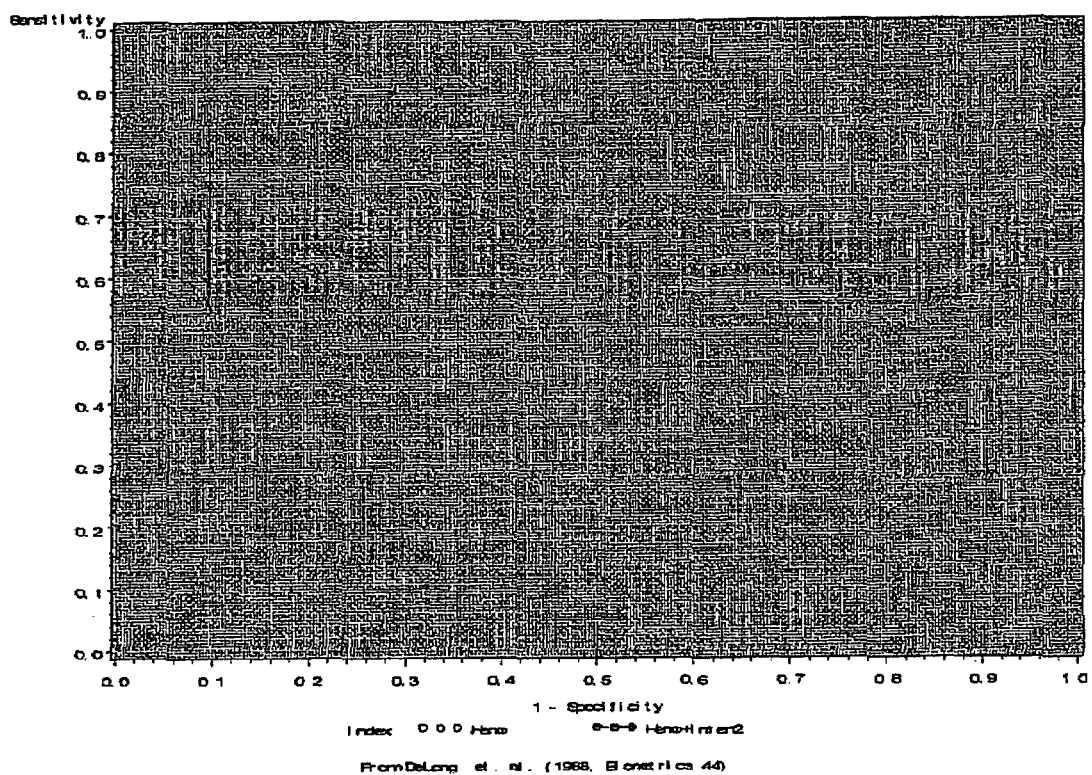
Figure 7E:
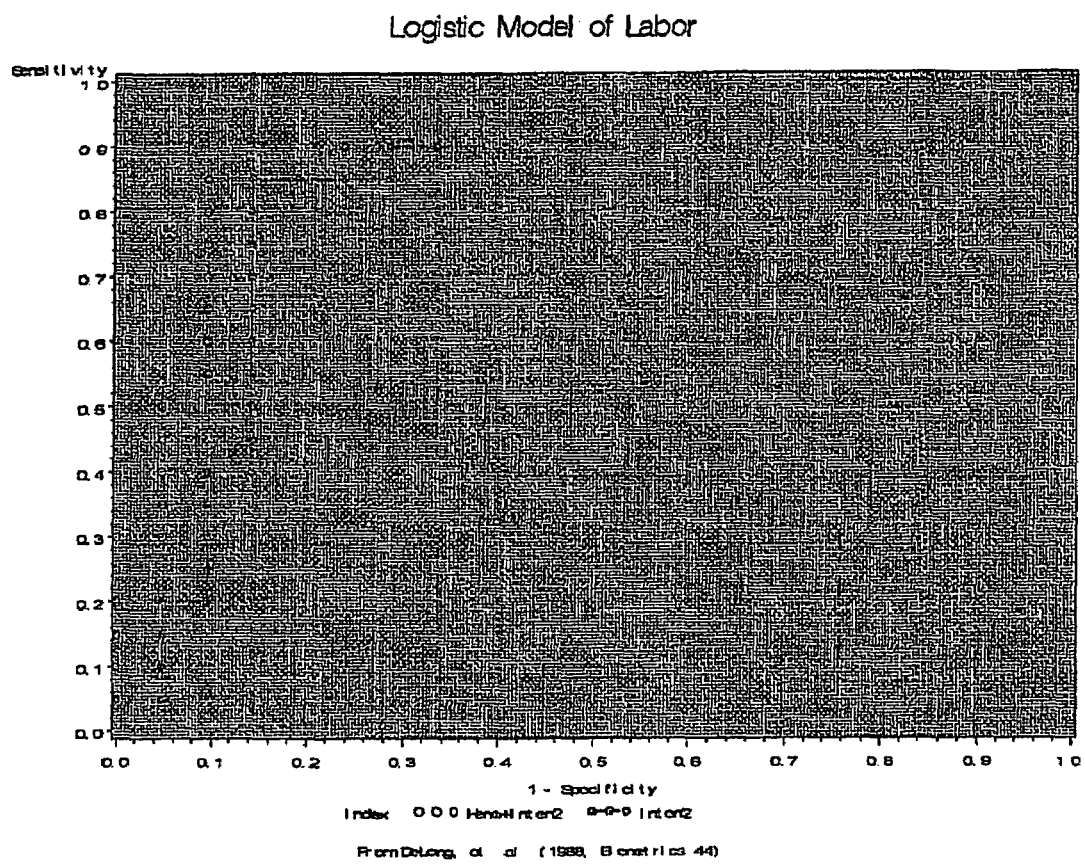
Figure 9:
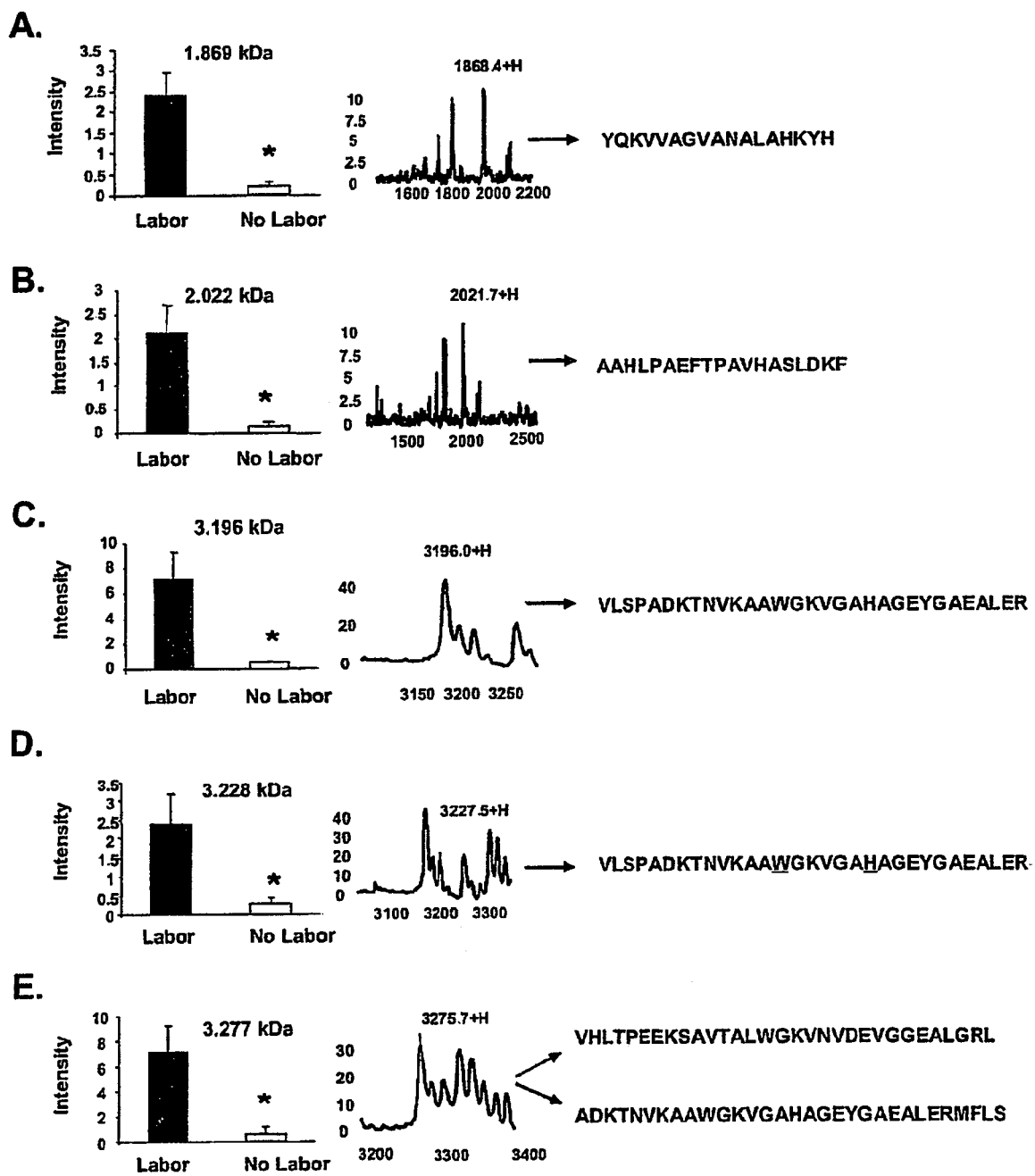
FIG. 9. Identities of cervicovaginal peaks. Several of the peaks that were significantly increased in cervicovaginal fluid from laboring women were identified using PCI-QTOF. Each portion of the figure corresponds to a specific peak and contains a histogram indicating the intensity differences between labor and no labor samples, a typical spectrum, and the amino acid sequence of the peak. The 1.869 kDa peak (FIG. 9A-SEQ ID NO: 10) and 1 peptide contained in the 3.277 kDa peak (FIG. 9E-Top peptide SEQ ID NO: 12; bottom peptide SEQ ID NO: 11) were identified as fragments of β-chain hemoglobin, and the 3.196 kDa peak (FIG. 9C-SEQ ID NO: 7) and the 3.228 kDa peak (FIG. 9D-SEQ ID NO: 8) have identical amino acids sequences, but the increased MW of the 3.228 kDa peak is due to oxidized tryptophan and histidine residues. 2.022 kDa peak (FIG. 9B-SEQ ID NO: 9), the 3.196 kDa peak (FIG. 9C-SEQ ID NO: 7), the 3.228 kDa peak (FIG. 9D-SEQ ID NO: 8), were all identified as fragments of α-chain hemoglobin. The underlined residues in the 3.228 kDa fragment are oxidized.

The hemoglobin levels of samples from the subjects of the previous Examples, and from the subjects recruited in the present Example, were tested using the Chemstrip 6® (Roche) urine multi-parameter test strip. A correlation between the total amount of hemoglobin in the samples and the labor status of the subjects was observed. Logistic regression models were then used to determine the best diagnostic combination, among the Chemstrip test and the SELDI peak intensity values of the 1.869 kDa and 3.198 kDa peaks. The best diagnostic test was found to be the combination of the Chemstrip results and the intensity of the 1.869 kDa peak, which increased sensitivity from 61.9% to 90.5% and improved specificity from 84.7% to 89.7%, relative to the 1.869 kDa peak alone, as shown by ROC (receiver operating characteristic) curves (FIG. 7A-B). Using this test, 90.5% of the subjects in labor and 89.7% of the subjects not in labor were correctly identified. The raw data from the analyses is depicted in FIG. 8. The following model was found to have the optimum predictive power:

$$ln[pr(\text{labor})/\{1-pr(\text{labor})\} 2.81-1.01(x)-1.51(y),$$

wherein p=the probability of being in labor
x=the Chemstrip score, as defined above; and
y=the intensity of the 1.869 kDa peak.

Thus, accurate diagnostic methods for detecting and predicting labor in both term and preterm pregnant subjects can be designed, using the peptides of the present invention.

EXAMPLE 7

Two of the Labor Markers Exhibit Structures of Biologically Active Peptides

Materials and Experimental Methods

Peptide Synthesis

Peptide synthesis was performed by Genemed Synthesis.

Results

Two of the fragments identified in the above analysis were synthesized; namely, amino acids 110-128 of α-chain hemoglobin (SEQ ID No: 9), and amino acids 130-146 of β-chain hemoglobin (SEQ ID No: 10). The first fragment exhibited a structure of a peptide with bradykinin potentiating activity.

These findings show that a peptide containing amino acids 110-128 of α-chain hemoglobin increases vascular permeability.

EXAMPLE 8

Identification of Additional Labor Markers from Previous Examples

The protocol described in Example 2 is used to identify the other labor markers depicted in FIGS. 2A and 4A. Identification of these markers enables the use of additional tests such as any of various known immuno-assays, to assess their concentrations, thus modifying the diagnostic tests of the present invention.

EXAMPLE 9

Isolation and Identification of Additional Labor Markers

SELDI, mass spectrometry, and CART analysis are used to isolate and identify additional labor markers as described in Examples 1-4. The additional markers are used to further enhance the sensitivity and specificity of the diagnostic algorithms of the present invention.

EXAMPLE 10

Multivariate Statistical Analysis of Labor Markers

CART analysis is used to analyze the marker proteins identified in Examples 1-5 in combination with maternal age, gestational age, reproductive history, serum hCG level, and/or other known factors, to improve their accuracy in predicting and/or detecting the onset of labor.

EXAMPLE 11

Use of Multivariate Statistical Analysis to Identify Additional Labor Markers

CART analysis is performed on candidate marker protein concentrations in combination with maternal age, gestational age, reproductive history, serum hCG level, and/or other known factors. This analysis will identify marker proteins that are diagnostic of labor when considered in combination with the additional factor(s), even though the concentration of the marker protein, when considered alone, may have less or no diagnostic value.

EXAMPLE 12

The 2.022 kDa Peptide Exhibits Uterotonic Potentiating Activity

Materials and Experimental Methods

Gels for Smooth Muscle Cells Activation Bioassay

PA gels of controlled stiffness were coated with a nearly constant collagen level ($5 \times 10^2$ ng/cm$^2$) as assessed by fluorescent collagen intensities. Nanometer-scale gel stiffness was measured by AFM, using cantilever tips with radii of curvature <50 nm.

Bioassay of Smooth Muscle Activating Peptides

To assess the ability of peptides found in cervicovaginal fluid to activate smooth muscle cells, rat aorta-derived A7R5 vascular smooth muscle cells (A7R5; ATCC, Manassas, Va.) were plated onto polyacrylamide gel surfaces (34 kPa) with collagen type 1 (BD Biosciences, San Diego) and covalently pre-attached to the gel surface by sulpho-SANPAH (Pierce, Rockland, Ill.), providing a quantitative and reproducible uterotonics activity assay. Cells were permitted to adhere to the surface for 30 minutes, then were incubated at 37° C. for 4 hours with bradykinin (0-1 µM, Sigma-Aldrich, St. Louis, Mo.), oxytocin (0-1 µM, Sigma-Aldrich) or the prostanoid PGF2α (0-0.1 µM, Sigma-Aldrich) +/− varying doses of the 2.022 kDa peptide or the control peptide, in which the sequence was scrambled, after which they were observed on a Nikon TE300 inverted microscope with an attached cooled CCD camera. Cellular area measurements were made using Image1 software 1.321 (NIH) from a large number of cells (n>50/culture). Data was fit to a hyperbolic expression using a least squared method, with the half-saturation constant ($IC_{50}$) representing the intermediate set-point for the system.

In other assays, human uterine smooth muscle cells (Ut-SMC) were treated with 10 nM bradykinin, 0.5 µM prostaglandin 2α (PGF2α), or 50 nM oxytocin, in the absence or presence of 5 µg/ml of the 2.022 kDa peptide, or with 10 µg/ml peptide alone. Numbers of contracted cells (exhibiting a shorter, rounded morphology) were quantitated.

Oxytocin Potentiation Assay

The oxytocin potentiation tissue assay was performed by MDS Pharma Service, Taipei, Taiwan. Briefly, pregnant Wistar rat uteri (325±25 g) were isolated and suspended in an isometric tissue bath containing Krebs buffer, pH 7.4. The uteri were treated with 1 nM oxytocin +/− the 2.022 kDa peptide (100 µM), the control peptide (100 µM), distilled water, or phosphoramidon (30 µM), which inhibits oxytocin breakdown as a positive control, and incubated for 5 minutes at 32 C. Tissue reactivity (n=2) was quantitatively assessed after five minutes by recording isometric contractions (gm changes).

Results

Figure 10:
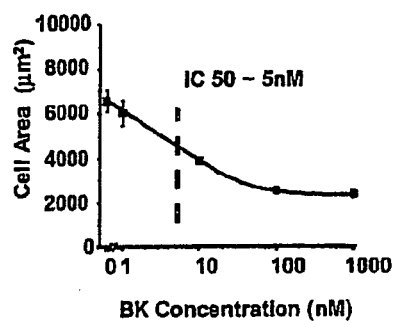
FIG. 10. The 2.022 kDa fragment potentiates the action of bradykinin, oxytocin and PGF2-α on rat aortic smooth muscle cells (A). Bradykinin (BK) administration elicited a dose-dependent decrease in cell area with an $IC_{50}$ of 5 nM. The potentiation peptide (PP) augmented the 5 nM BK response by dramatically decreasing cell area compared to 5 nM BK in the presence of control peptide (CP), (P<0.0001). Oxytocin (OT) administration elicited a dose-dependent decrease in cell area with an $IC_{50}$ of 8 nM. The potentiation peptide (PP) augmented the 10 nM OT response by dramatically decreasing cell area compared to 10 nM OT in the presence of control peptide (CP), (P<0.0011). PGF2-α administration elicited a dose-dependent decrease in cell area with an $IC_{50}$ of 0.56 nM. The potentiation peptide (PP) augmented the 0.56 nM PG response by dramatically decreasing cell area compared to 0.56 nM PG in the presence of control peptide (CP), (P<0.0001). Asterisks indicate statistically significant differences (P<0.05) between the CP and PP in all treatment groups.
Figure 10:
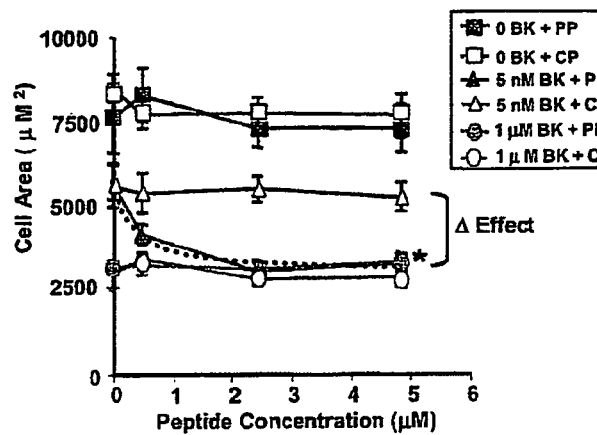
Figure 10:
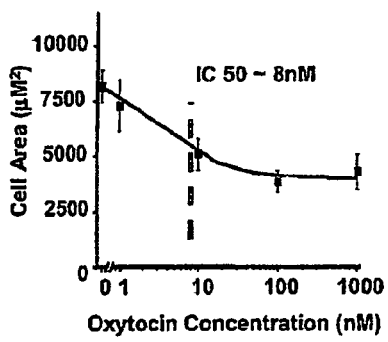
Figure 10:
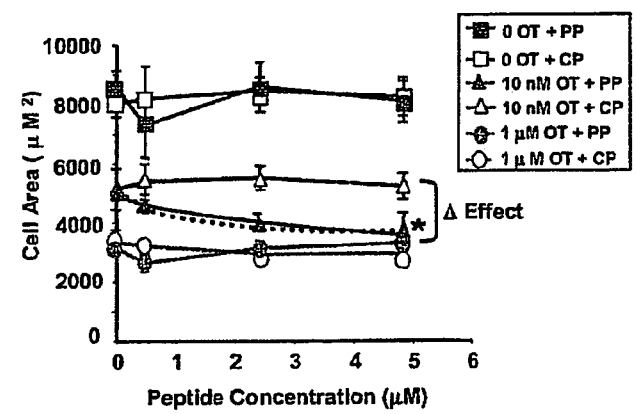
Figure 10:
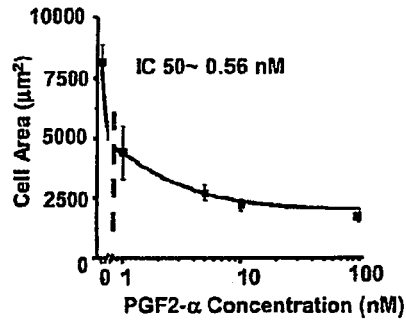
Figure 10:
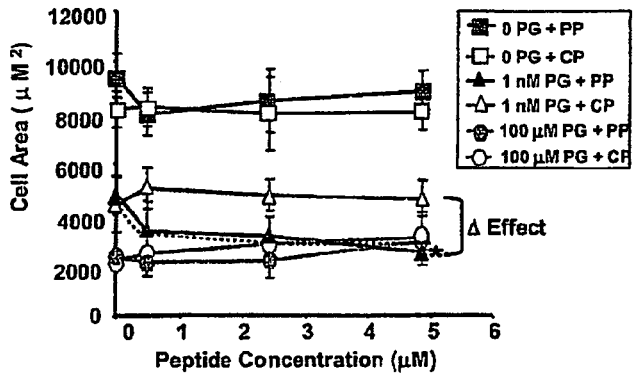

To determine whether the 2.022 kDa fragment, amino acids 110-128 of α-chain hemoglobin (SEQ ID No: 9), acts as a bradykinin potentiation factor, agonist-induced cell shape change studies were performed on bradykinin-treated and untreated vascular smooth muscle cells. To measure cell contractility, A7R5 cells were plated on collagen-coated hydrogels and were permitted to adhere and spread to a certain cell area, which is dependent upon myosin contractility. Bradykinin treatment resulted in a hyper-contractile cell morphology, which significantly limited cell spreading with an $IC_{50}$ of 5 nM. When the 2.022 kDa peptide (PP) or a control peptide (CP) was added together with a half-saturation dose of bradykinin (5 nM), the 2.022 kDa peptide augmented the bradykinin response, and cell area was decreased maximally (P 0.0004; half-saturation effect of the peptide: 9.346 µM) (FIG. 10A). By contrast, the decrease in cell area elicited by maximal doses of bradykinin (1 µM) was not affected by the 2.022 kDa peptide. Neither the 2.022 kDa peptide nor the control peptide had an effect on cell area when administered without bradykinin. As expected, the control peptide did not affect the bradykinin response (P=0.95).

To determine whether the 2.022 kDa peptide enhances the effects of other agents that promote smooth muscle contraction, the effect of the peptide on oxytocin- and PGF2α-induced contraction was determined. Oxytocin and PGF2≠0 decreased cell area with IC 50s of 8 nM and 1 nM, respectively (FIG. 10B-C). This decrease in cell area was enhanced by sub-µM amounts of the 2.022 kDa peptide, with maximal enhancement occurring at approximately half the saturation dose of oxytocin or PGF2α (FIG. 2 B and C, see Δ effect, P=0.0011 and P<0.0001, respectively).

Figure 11:
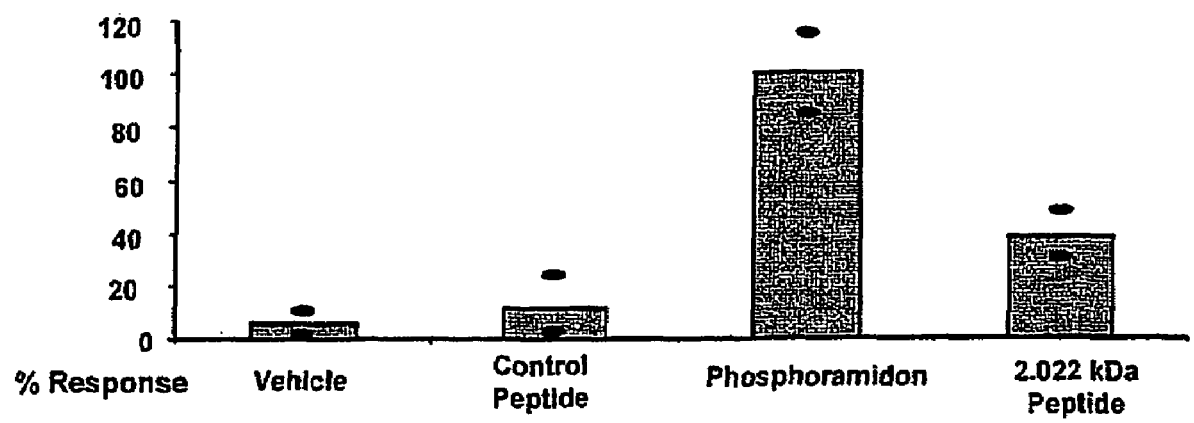
FIG. 11. The 2.022 kDa α-Hb fragment potentiates the action of oxytocin on rat uterus. Pregnant Wistar rat uteri were treated with 1 nm Oxytocin +/−100 μM of the 2.022 kDa peptide or a control peptide, 0.1 ml distilled water (vehicle) or 30 μM phosphoramidon (positive control). The 2.022 kDa peptide increased uterine tissue contractility in the presence of oxytocin by approximately 30% compared to control peptide in the presence of oxytocin.

In addition, the ability of the 2.022 kDa peptide to augment the effects of oxytocin on uterine tissue was evaluated utilizing an isometric tissue bath. Administration of 30 µM phosphoramidon, a protease inhibitor, served as the positive control. The 2.022 kDa peptide (100 µM) increased uterine contraction in the presence of oxytocin by 30% compared to the negative controls (distilled water or 100 µM of the control peptide), as depicted in FIG. 11.

These results show that the 2.022 kDa peptide exhibits uterotonic potentiating activity, demonstrating that this peptide plays a role in labor induction. Thus, an antagonist of this peptide is useful in preventing labor.

EXAMPLE 13

Identification of Inhibitors of the 2.022 kDa Peptide

Inhibitors of the 2.022 kDa peptide are produced by designing and producing small molecule inhibitors, using one of the methods described in, for example, Tanuma S et al (Biol Pharm Bull 27(7): 968-73, 2004; Raimundo B et al (J Med Chem 47(12): 3111-30, 2004; Wang J et al, Proc Natl Acad Sci USA 97(13): 7124-9; 2000; and Huang J et al, (Proc. Natl. Acad. Sci. USA 94: 13396-13401, 1997). Alternatively, antibodies are raised to the 2.022 kDa peptide. Alternatively, a biological target of the 2.022 kDa peptide is identified, and molecules that inhibit interaction between the peptide and its target are identified, using one of the above methods.

EXAMPLE 14

Testing Inhibitors of the 2.022 kDa Peptide in an Animal Model for Inhibition of Induction of Labor The inhibitors of the 2.022 kDa peptide identified in the previous Example are tested in an animal model for inhibition of induction of labor, such as that described in Gross G et al, Am J Physiol Regul Integr Comp Physio 278(6): R1415-23, 2000; Dieni S et al, J Neuropathol Exp Neuro 63(12): 1297-309, 2004; or Chellman G et al, Reprod Toxicol 18(2): 285-93, 2004. Inhibition of induction of labor in the animal model indicates that the peptide and variants and homologues thereof are useful in inhibiting labor in human and animal subjects.38

What is claimed is:

1. A method of predicting or detecting labor in a female subject, comprising
   a. determining an amount of a first peptide in a biological sample of said female subject, said first peptide having the amino acid sequence set forth in SEQ ID No: 10;
   b. comparing said amount of said first peptide to a reference standard for said first peptide;
   c. determining an amount of a second peptide, said second peptide having the amino acid sequence set forth in SEQ ID No: 7, wherein said amount is an amount in said biological sample or an additional biological sample of said female subject; and
   d. comparing said amount of said second peptide to a reference standard for said second peptide,
   whereby if:
      (i) both
         (i a) said amount of said first peptide is higher than an upper limit of a range defined by said reference standard for said first peptide; and
         (i b) said amount of said second peptide is higher than an upper limit of a range defined by said reference standard for said second peptide,
      then said female subject is in labor;
   and if:
      (ii) both
         (ii a) said amount of said first peptide is higher than said upper limit of said range defined by said reference standard for said first peptide; and
         (ii b) said amount of said second peptide is lower than a lower limit of said range defined by said reference standard for said second peptide,
      then said female subject is not in labor.

2. The method of claim 1, wherein said first peptide comprises an oxidized amino acid.

3. The method of claim 1, wherein said second peptide comprises an oxidized amino acid.

4. The method of claim 1, whereby at least one of (a) the step of determining said amount of said first peptide; and (b) the step of determining said amount of said second peptide comprises an immunological assay.

5. The method of claim 1, wherein at least one of (a) said biological sample and (b) said additional biological sample is a cervicovaginal secretion.

6. The method of claim 1, wherein said labor is a preterm labor.

* * * * *

SEQUENCE LISTING

<160> NUMBER OF SEQ ID NOS: 12

<210> SEQ ID NO 1
<211> LENGTH: 22
<212> TYPE: PRT
<213> ORGANISM: Homo sapiens

<400> SEQUENCE: 1

Asp Ala His Lys Ser Glu Val Ala His Arg Phe Lys Asp Leu Gly Glu
1               5                   10                  15

Glu Asn Phe Lys Ala Leu
            20

<210> SEQ ID NO 2
<211> LENGTH: 29
<212> TYPE: PRT
<213> ORGANISM: Homo sapiens

<400> SEQUENCE: 2

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu
            20                  25

<210> SEQ ID NO 3
<211> LENGTH: 32
<212> TYPE: PRT
<213> ORGANISM: Homo sapiens

<400> SEQUENCE: 3

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

<210> SEQ ID NO 4
<211> LENGTH: 31
<212> TYPE: PRT
<213> ORGANISM: Homo sapiens

<400> SEQUENCE: 4

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg
            20                  25                  30

<210> SEQ ID NO 5
<211> LENGTH: 31
<212> TYPE: PRT
<213> ORGANISM: Homo sapiens
<220> FEATURE:
<221> NAME/KEY: Contains 1 oxidized amino acid
<222> LOCATION: (1)..(31)

<400> SEQUENCE: 5

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg
            20                  25                  30

<210> SEQ ID NO 6

```
<211> LENGTH: 31
<212> TYPE: PRT
<213> ORGANISM: Homo sapiens
<220> FEATURE:
<221> NAME/KEY: oxidized amino acid
<222> LOCATION: (15)..(15)
<220> FEATURE:
<221> NAME/KEY: oxidized amino acid
<222> LOCATION: (21)..(21)

<400> SEQUENCE: 6

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg
            20                  25                  30

<210> SEQ ID NO 7
<211> LENGTH: 31
<212> TYPE: PRT
<213> ORGANISM: Homo sapiens

<400> SEQUENCE: 7

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg
            20                  25                  30

<210> SEQ ID NO 8
<211> LENGTH: 31
<212> TYPE: PRT
<213> ORGANISM: Homo sapiens
<220> FEATURE:
<221> NAME/KEY: oxidized amino acid
<222> LOCATION: (15)..(15)
<220> FEATURE:
<221> NAME/KEY: oxidized amino acid
<222> LOCATION: (21)..(21)

<400> SEQUENCE: 8

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg
            20                  25                  30

<210> SEQ ID NO 9
<211> LENGTH: 19
<212> TYPE: PRT
<213> ORGANISM: Homo sapiens

<400> SEQUENCE: 9

Ala Ala His Leu Pro Ala Glu Phe Thr Pro Ala Val His Ala Ser Leu
1               5                   10                  15

Asp Lys Phe

<210> SEQ ID NO 10
<211> LENGTH: 17
<212> TYPE: PRT
<213> ORGANISM: Homo sapiens

<400> SEQUENCE: 10

Tyr Gln Lys Val Val Ala Gly Val Ala Asn Ala Leu Ala His Lys Tyr
1               5                   10                  15

His
```

```
<210> SEQ ID NO 11
<211> LENGTH: 31
<212> TYPE: PRT
<213> ORGANISM: Homo sapiens

<400> SEQUENCE: 11

Ala Asp Lys Thr Asn Val Lys Ala Ala Trp Gly Lys Val Gly Ala His
1               5                   10                  15

Ala Gly Glu Tyr Gly Ala Glu Ala Leu Glu Arg Met Phe Leu Ser
            20                  25                  30

<210> SEQ ID NO 12
<211> LENGTH: 31
<212> TYPE: PRT
<213> ORGANISM: Homo sapiens

<400> SEQUENCE: 12

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu
            20                  25                  30
```